US010635833B2

(12) United States Patent
Kaditz et al.

(10) Patent No.: US 10,635,833 B2
(45) Date of Patent: Apr. 28, 2020

(54) UNIFORM-FREQUENCY RECORDS WITH OBSCURED CONTEXT

(71) Applicant: Q Bio, Inc, Millbrae, CA (US)

(72) Inventors: Jeffrey Howard Kaditz, Wilson, WY (US); Andrew Gettings Stevens, New York, NY (US); David Grijalva, San Francisco, CA (US)

(73) Assignee: Q Bio, Inc., San Carlos, CA (US)

( * ) Notice: Subject to any disclaimer, the term of this patent is extended or adjusted under 35 U.S.C. 154(b) by 407 days.

(21) Appl. No.: 15/499,004

(22) Filed: Apr. 27, 2017

(65) Prior Publication Data
US 2017/0228557 A1   Aug. 10, 2017

Related U.S. Application Data

(63) Continuation of application No. 15/262,001, filed on Sep. 11, 2016, now Pat. No. 9,665,734.
(Continued)

(51) Int. Cl.
*G06F 21/62*   (2013.01)
*G06F 16/11*   (2019.01)
(Continued)

(52) U.S. Cl.
CPC ........ *G06F 21/6227* (2013.01); *G06F 16/122* (2019.01); *G06F 19/00* (2013.01);
(Continued)

(58) Field of Classification Search
None
See application file for complete search history.

(56) References Cited

U.S. PATENT DOCUMENTS

| 4,729,892 A | 3/1988 | Beall |
| 5,486,762 A | 1/1996 | Freedman et al. |

(Continued)

FOREIGN PATENT DOCUMENTS

| EP | 3093677 | 11/2016 |
| WO | WO-201405275 | 12/2014 |

(Continued)

OTHER PUBLICATIONS

"Robust Multiresolution Alignment of MRI Brain Volumes, Other Description Feb. 6, 2017", 705-715.
(Continued)

*Primary Examiner* — Hung D Le
(74) *Attorney, Agent, or Firm* — Aurora Consulting LLC; Steven E. Stupp; Ashley Sloat

(57) ABSTRACT

A computer system may perform substitutions for fields in a set of records, where performing a given substitution involves replacing a field in the set of records with a replacement field, and the substitutions remove the context information in the set of records while maintaining relevance of the set of records. Then, the computer system may generate an artificial set of records based, at least in part, on the set of records, where a given artificial record includes one or more modified portions of the set of records. Next, the computer system may combine the set of records and the artificial set of records into a second set of records, where at least some phrases or values in the second set of records are uniformly distributed.

20 Claims, 15 Drawing Sheets

Related U.S. Application Data

(60) Provisional application No. 62/217,804, filed on Sep. 12, 2015.

(51) Int. Cl.
    *G06F 19/00*     (2018.01)
    *G06F 21/60*     (2013.01)
    *G16H 10/60*     (2018.01)
    *H04L 9/08*     (2006.01)

(52) U.S. Cl.
CPC .......... *G06F 19/328* (2013.01); *G06F 21/604* (2013.01); *G06F 21/6218* (2013.01); *G06F 21/6254* (2013.01); *G06F 19/321* (2013.01); *G06F 2221/2151* (2013.01); *G16H 10/60* (2018.01); *H04L 9/0841* (2013.01); *H04L 2463/082* (2013.01)

(56) References Cited

U.S. PATENT DOCUMENTS

| | | | |
|---|---|---|---|
| 5,793,210 A * | 8/1998 | Pla | G01R 33/3854 |
| | | | 324/318 |
| 6,084,408 A | 7/2000 | Chen | |
| 6,148,272 A * | 11/2000 | Bergstrom | A61N 5/1031 |
| | | | 250/363.04 |
| 6,392,409 B1 | 5/2002 | Chen | |
| 6,678,669 B2 | 1/2004 | Lapointe | |
| 7,924,002 B2 | 4/2011 | Lu | |
| 7,940,927 B2 | 5/2011 | Futa | |
| 7,974,942 B2 | 7/2011 | Pomroy | |
| 8,432,165 B2 | 4/2013 | Weiger Senften | |
| 8,502,532 B2 | 8/2013 | Assmann | |
| 8,686,727 B2 | 4/2014 | Reddy | |
| 8,723,518 B2 * | 5/2014 | Seiberlich | G01R 33/543 |
| | | | 324/307 |
| 8,736,265 B2 | 5/2014 | Boernert | |
| 9,513,359 B2 | 12/2016 | Koch | |
| 9,514,169 B2 | 12/2016 | Mattsson | |
| 2002/0155587 A1 | 10/2002 | Opalsky | |
| 2002/0177771 A1 | 11/2002 | Guttman | |
| 2003/0210043 A1 | 11/2003 | Freedman | |
| 2005/0137476 A1 * | 6/2005 | Weiland | G01R 33/4625 |
| | | | 600/416 |
| 2005/0181466 A1 | 8/2005 | Dambinova | |
| 2008/0065665 A1 | 3/2008 | Pomroy | |
| 2008/0081375 A1 * | 4/2008 | Tesiram | G01N 24/08 |
| | | | 436/57 |
| 2008/0082834 A1 | 4/2008 | Mattsson | |
| 2009/0315561 A1 | 12/2009 | Assmann | |
| 2010/0131518 A1 | 5/2010 | Elteto | |
| 2010/0142823 A1 | 6/2010 | Wang | |
| 2010/0177188 A1 | 7/2010 | Kishima | |
| 2010/0189328 A1 * | 7/2010 | Boernert | G01R 33/56375 |
| | | | 382/131 |
| 2010/0244827 A1 | 9/2010 | Hennel | |
| 2010/0306854 A1 | 12/2010 | Neergaard | |
| 2011/0095759 A1 | 4/2011 | Bhattacharya | |
| 2011/0166484 A1 | 7/2011 | Virta | |
| 2012/0124161 A1 | 5/2012 | Tidwell | |
| 2012/0203798 A1 * | 8/2012 | Gifford | G16H 10/60 |
| | | | 707/783 |
| 2013/0275718 A1 | 10/2013 | Ueda | |
| 2013/0294669 A1 | 11/2013 | El-Baz | |
| 2013/0338930 A1 | 12/2013 | Senegas | |
| 2014/0062475 A1 | 3/2014 | Koch | |
| 2014/0300490 A1 * | 10/2014 | Kotz | A61B 5/0028 |
| | | | 340/870.3 |
| 2014/0336998 A1 | 11/2014 | Cecchi | |
| 2015/0003706 A1 | 1/2015 | Eftestøl | |
| 2015/0032421 A1 * | 1/2015 | Dean | G06T 19/00 |
| | | | 703/1 |
| 2015/0040225 A1 | 2/2015 | Coates | |
| 2015/0089574 A1 | 3/2015 | Mattsson | |
| 2016/0007968 A1 | 1/2016 | Sinkus | |
| 2016/0127123 A1 | 5/2016 | Johnson | |
| 2017/0011514 A1 | 1/2017 | Westerhoff | |
| 2017/0038452 A1 | 2/2017 | Trzasko | |

FOREIGN PATENT DOCUMENTS

| | | |
|---|---|---|
| WO | WO-2014205275 | 12/2014 |
| WO | WO-2016073985 | 5/2015 |
| WO | WO-2015183792 | 12/2015 |
| WO | WO-21315183792 | 12/2015 |

OTHER PUBLICATIONS

"International Application Serial No. PCT/US2017/022842, International Search Report dated May 23, 2017, PCT search report May 23, 2017", 2 pgs.

"International Application Serial No. PCT/US16/040215, International Searh Report dated Sep. 19, 2016, Other Description Mar. 1, 2017", 2 pgs.

"International Application Serial No. PCT/US16/040215, Written Opinion dated Sep. 19, 2016, Other Description Mar. 1, 2017", 9 pgs.

"International Application Serial No. PCT/US16/040578, International Search Report dated Sep. 19, 2016, Other Description Mar. 1, 2017", 2 pgs.

"International Application Serial No. PCT/US16/51204, International Search Report dated Nov. 28, 2016, Other Description Mar. 1, 2017", 2 pgs.

"International Application Serial No. PCT/US16/040578, Written Opinion dated Sep. 19, 2016, Other Description Mar. 1, 2017", 9 pgs.

"International Application Serial No. PCT/US16/51204, Written Opinion dated Nov. 28, 2016, Other Description Mar. 1, 2017", 10 pgs.

"International Application Serial No. PCT/US2017/022842, Written Opinion dated May 23, 2017, PCT report opinion dated May 23, 2017", 4 pgs.

"Prosthetic Heart Valve Evaluation by Magnetic Resonance Imaging, Other Description Feb. 6, 2017", 300-305.

U.S. Appl. No. 15/169,719, filed May 31, 2016, Fast Scanning Based on Magnetic-Resonance History.

U.S. Appl. No. 15/089,571, filed Apr. 3, 2016, Field-Invariant Quantitative Magnetic-Resonance Signatures.

U.S. Appl. No. 15/299,337, filed Oct. 20, 2016, Population-Based Medical Rules Via Anonymous Sharing.

U.S. Appl. No. 15/362,808, filed Nov. 28, 2016, Tensor Field Mapping.

U.S. Appl. No. 15/362,813, filed Nov. 28, 2016, Rapid Determination of a Relaxation Time.

U.S. Appl. No. 15/461,429, filed Mar. 16, 2017, Iterative Medical Testing of Biological Samples.

Drescher et al., article titled "Longitudinal Screening Algorithm That Incorporates Change Over Time in CA125 Levels Identifies Ovarian Cancer Earlier Than a Single-Threshold Rule".

G. Schultz, "Magnetic Resonance Imaging with Nonlinear Gradient Fields: Signal Encoding and Image Reconstruction" Springer Verlag, New York, 2013), Chapter 2, pp. 1-10.

Gualda et al. SPIM-fluid: open source light-sheet based platform for high-throughput imaging. Biomed Opt Express (Nov. 1, 2015) vol. 6, No. 11, pp. 4447-4456, p. 4448 para 2-3, p. 4450, para 2.

Hasenkam et al., "Prosthetic Heart Valve Evaluation by Magnetic Resonance Imaging," European Journal of Cardio-thoracic Surgery 16 (1999) 300-305.

I. Kononenko "Machine learning for medical diagnosis: history, state of the art and perspective" Artificial Intelligence in Medicine 23 (2001) 21 pgs.

International Application Serial No. PCT/US2016/040215, International Preliminary Report on Patentability and Written Opinion dated Jan. 9, 2018.

"International Application Serial No. PCT/US2016/040215, International Search Report dated Sep. 19, 2016, PCT search report dated Mar. 1, 2017", 2 pgs.

(56) References Cited

OTHER PUBLICATIONS

"International Application Serial No. PCT/US2016/040215, Written Opinion dated Sep. 19, 2016, PCT report opinion dated Mar. 1, 2017", 9 pgs.

"International Application Serial No. PCT/US2016/040578, International Search Report dated Sep. 19, 2016, Other Description Mar. 1, 2017", 2 pgs.

"International Application Serial No. PCT/US2016/040578, Written Opinion dated Sep. 19, 2016, PCT report opinion dated Mar. 1, 2017", 9 pgs.

"International Application Serial No. PCT/US2016/051204, International Search Report dated Nov. 28, 2016, PCT search report dated Mar. 1, 2017", 2 pgs.

"International Application Serial No. PCT/US2016/051204, Written Opinion dated Nov. 28, 2016, PCT report opnion dated Mar. 1, 2017", 10 pgs.

"International Application Serial No. PCT/US2017/022842, International Search Report dated May 23, 2017, PCT search report dated May 23, 2017", 2 pgs.

"International Application Serial No. PCT/US2017/022842, Written Opinion dated May 23, 2017, PCR report opinion dated May 23, 2017", 4 pgs.

"International Application Serial No. PCT/US2017/022911, International Search Report dated Jul. 19, 2017, PCT search report dated Jul. 19, 2019", 4 pgs.

"International Application Serial No. PCT/US2017/022911, Written Opinion dated Jul. 19, 2017, PCT report opnion dated Jul. 19, 2017", 10 pgs.

"International Application Serial No. PCT/US2017/035071, International Search Report dated Aug. 22, 2017, PCT search report Aug. 22, 2017", 2 pgs.

"International Application Serial No. PCT/US2017/035071, Written Opinion dated Aug. 22, 2017, PCT report opinion dated Aug. 22, 2017", 7 pgs.

"International Application Serial No. PCT/US2017/035073, International Search Report dated Aug. 11, 2017, PCT search report dated Aug. 11, 2017", 2 pgs.

"International Application Serial No. PCT/US2017/035073, Written Opnion dated Aug. 11, 2017, PCT report opinion dated Aug. 11, 2017", 6 pgs.

"Kwan et al: "MRI Simulation-Based Evaluation of Image-Processing and Classification Methods" IEEE Transactions on Medical Imaging. vol. 18 No. 11, Nov. 1999," 13 pgs.

"Siemens. Magnetic Resonance Imaging. (Dec. 2012) [retrieved on Jun. 27, 2017, https://w5.siemens.com/web/ua/ru/medecine/detection_diagnosis/agnetic_resonans/035-15-MRI-scaners/Documents/mri-magnetom-family_brochure-00289718.pdf] p. 6-8, 13, 15-16".

"Nestares et al., "Robust Multiresolution Alignment of MRI Brain Volumes," Magnetic Resonance in Medicine 43:705-715 (2000), Other Description Feb. 6, 2017", 705-715.

* cited by examiner

SET OF
RECORDS
600

| REAL MEDICAL RECORDS 610-1 | ARTIF. MEDICAL RECORDS 612-1 | ARTIF. MEDICAL RECORDS 612-2 | REAL MEDICAL RECORDS 610-2 | ARTIF. MEDICAL RECORDS 612-3 | REAL MEDICAL RECORDS 610-3 | ... |

FIG. 6

UNIFORM-FREQUENCY RECORDS WITH OBSCURED CONTEXT

CROSS-REFERENCE TO RELATED APPLICATION

The is application claims priority under 35 U.S.C. 120 as a Continuation of U.S. patent application Ser. No. 15/262,001, entitled "Uniform-Frequency Records with Obscured Context," filed Sep. 11, 2016, which claims priority under 35 U.S.C. § 119(e) to: U.S. Provisional Application Ser. No. 62/217,804, entitled "System and Method for Separate Storage of Identities and Sensitive Data," filed on Sep. 12, 2015, the contents of both of which are herein incorporated by reference.

BACKGROUND

Field

The described embodiments relate to techniques for securing records. In particular, the described embodiments relate to techniques for securing records by elimination context information with substitutions, and/or by adding additional artificial records in order to ensure a uniform distribution of at least some phrases or values.

Related Art

While the large datasets can facilitate a wide variety of value-added services, such datasets are increasingly vulnerable to unauthorized viewing and theft. In addition to significant financial harm, these criminal activities are particularly devastating in the case of sensitive information, such as medical records for patients. Consequently, many countries have passed stringent laws and regulations in attempt to protect medical records. For example, in the United States, Protected Health Information (PHI) in general is covered by the Health Insurance Portability and Accountability Act (HIPAA) while electronic PHI (such as medical records) is covered by the HIPAA Security Rule (SR).

Instead of mandating particular security infrastructure and techniques, the HIPAA SR provides a flexible framework that requires an organization that has access to or that handle electronic PHI to continuously assess and adapt their security procedures based on the maturity of the organization, the security risks, and the approaches used by similar organizations. In principle, this regulatory framework helps organizations dynamically improve their handling of electronic PHI. In general encryption is a widely used security technique in most organizations' HIPAA plans. For example, patient medical records and related sensitive information are often encrypted using symmetric or asymmetric key encryption, and/or using a cryptographic hashing function.

As the power of widely available computing systems has increased, the encryption key length has also been increased to make it more difficult (and, thus, more time consuming) to break the encryption. For example, most organizations use at least 128 or 256-bit encryption keys. While longer encryption keys can increase the security of the electronic PHI, there is usually a cost in the form of increased encryption/decryption times and processing requirements. For small medical records, these costs are usually negligible. However, for very large medical records, such as those that include medical images, the encryption/decryption times and processing requirements can be prohibitive.

More fundamentally, and as embodied in the HIPAA law, the use of encryption does not, per se, ensure the security of electronic PHI. Indeed, there have bees routine breaches of security in datasets that were, in principle, secured using encryption. In the context of healthcare, the perceived lack of security undermines patient trust and, thus, adversely impact patient satisfaction.

SUMMARY

The described embodiments relate to a computer system that secures a set of records. This computer system includes: a processor that executes a program module; and memory that stores the program module. During operation, the processor executing the program module performs substitutions for fields in the set of records, where performing a given substitution involves replacing a field in the set of records with a replacement field, and the substitutions remove context information in the set of records while maintaining relevance of the set of records. Then, the processor may generate an artificial set of records based, at least in part, on the set of records, where a given artificial record includes one or more modified portions of the set of records. Next, the processor may combine the set of records and the artificial set of records into a second set of records, where at least some phrases or values in the second set of records are uniformly distributed.

Note that the replacement field may include random or pseudorandom alphanumeric information.

Moreover, the set of records and the artificial set of records may be randomly or pseudo-randomly ordered in the second set of records.

Furthermore, the substitutions may be predefined. Alternatively or additionally, the substitutions may be determined based on information value of the fields in the set of records. For example, the substitutions may be determined based on a cardinality of the fields in the set of records.

In some embodiments, the processor reorders fields that include timestamps in the set of records. These fields may include one or more words or second values.

Additionally, the processor may modify imaging data in the set of records based on imaging instructions and an invariant signature that predicts responses of voxels in at least an individual.

Another embodiment provides a computer-program product for use with the computer system. This computer-program product includes instructions for at least some of the operations performed by the computer system.

Another embodiment provides a method for securing the set of records.

The preceding summary is provided as an overview of some exemplary embodiments and to provide a basic understanding of aspects of the subject matter described herein. Accordingly, the above-described features are merely examples and should not be construed as narrowing the scope or spirit of the subject matter described herein in any way. Other features, aspects, and advantages of the subject matter described herein will become apparent from the following Detailed Description, Figures, and Claims.

BRIEF DESCRIPTION OF THE FIGURES

FIG. 6 is a drawing illustrating securing a set of records in the system in FIG. 1 in accordance with an embodiment of the present disclosure.

Note that like reference numerals refer to corresponding parts throughout the drawings. Moreover, multiple instances of the same part are designated by a common prefix separated from an instance number by a dash.

DETAILED DESCRIPTION

In order to secure a set of records, a computer system may selectively remove context information and ensure uniform distributions of at least some phrases or values in the set of records. In particular, the computer system may perform substitutions for fields in the set of records, where performing a given substitution involves replacing a field in the set of records with a replacement field, and the substitutions remove the contest information in the set of records while maintaining relevance of the set of records. Then, the computer system may generate an artificial set of records based, at least in part, on the set of records, where a given artificial record includes one or more modified portions of the set of records. Next, the computer system may combine the set of records and the artificial set of records into a second set of records, where at least some phrases or values in the second set of records are uniformly distributed.

This security technique may enhance the security of the set of records without incurring significant processing and/or latency cost. For example, the security technique may secure the set of records without requiring the use of an encryption technique (which can be prohibitive when the set of records are large). Consequently, the security technique may improve user trust in the aggregation and use of the set of records to provide value-added services so the users, and thus may improve the overall user experience.

In the discussion that follows, an individual or a user may be a person. Moreover, the security technique may be used by any type of organization, such as a business, which should be understood to include for-profit corporations, non-profit corporations, groups (or cohorts) of individuals, sole proprietorships, government agencies, partnerships, etc. While the security technique may be used in a wide variety of applications, in the discussion that fellows the security technique is used in healthcare to secure medical records.

Furthermore, in the discussion that follows, electronic devices and/or components in a system that includes the computer system may communicate using a wide variety of communication protocols. For example, the communication may involve wired or wireless communication. Consequently, the communication protocols may include: an Institute of Electrical and Electronics Engineers (IEEE) 802.11 standard (which is sometimes referred to as 'Wi-Fi®,' from the Wi-Fi Alliance of Austin, Tex.), Bluetooth® (from the Bluetooth Special Interest Group of Kirkland, Wash.), another type of wireless interface (such as another wireless-local-area-network interface), a cellular-telephone communication protocol (e.g., a 3G/4G/5G communication protocol, such as UMTS, LTE) an IEEE 802.3 standard (which is sometimes referred to as 'Ethernet'), etc. In the discussion that follows, Ethernet and Wi-Fi and/or a cellular telephone communication protocol are used as illustrative examples.

Figure 1:
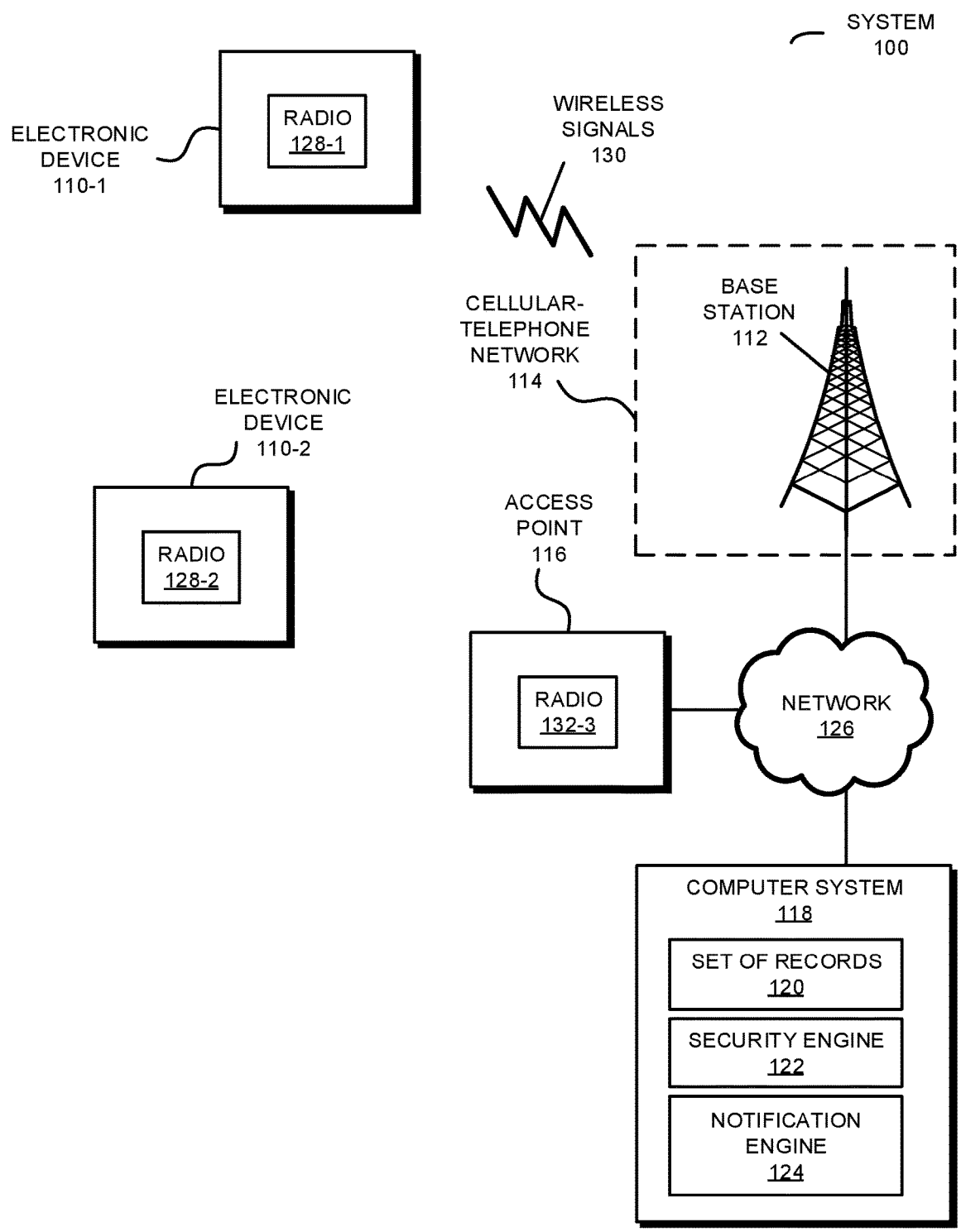
FIG. 1 is a block diagram illustrating a system that secures a set of records in accordance with an embodiment of the present disclosure.

Communication among electronic devices is shown in FIG. 1, winch presents a block diagram illustrating a system 100 that secures a set of records. In particular, system 100 includes one or more electronic devices 110 (such as cellular telephones or portable electronic devices, computers, etc.), optional base station 112 in cellular-telephone network 114, optional access point 116, and computer system 118 (which are sometimes collectively referred to as 'components' in system 100). Moreover, computer system 118 may include: a set of records 120 (winch may be stored in memory or a computer-readable medium, which is sometimes referred to as a 'biovault'), a security engine (or module) 122 and a notification engine (or module) 124. In some embodiments, the set of records 120 includes a block chain, i.e., a distributed database that maintains a continuously growing list of records (with data, individual transactions, the results of any blockchain executables and/or programs, as well as timestamps and links to one or more previous blocks) secured from tampering and revision. Therefore, changes to the set of records 120 may be appended to the existing set of records 120.

Note that components in system 100 may communicate with each other via a network 126, such as the Internet, a cellular-telephone network and/or a wireless local area network (WLAN). In embodiments where the communication involves wireless communication, the wireless communication includes: transmitting advertising frames on wireless channels, detecting another component in system 100 by scanning wireless channels, establishing connections (for example, by transmitting association requests), and/or transmitting and receiving packets (which may include information for inclusion in the set of records 120, requests for access to information in the set of records 120, notifications, etc.).

Moreover, as described further below with reference to FIG. 15, electronic devices 110, optional base station 112, optional access point 116 and computer system 118 may include subsystems, such as a networking subsystem, a memory subsystem and a processor subsystem. In addition, electronic devices 110, optional base station 112, optional access point 116 and computer system 118 may include radios 128 in the networking subsystems. More generally, the components can include (or can be included within) any electronic devices with the networking subsystems that enable these components to communicate with each other. Note that wireless communication can compose transmitting advertisements on wireless channels to enable a pair of components to make initial contact or detect each other, followed by exchanging subsequent data/management frames (such as association requests and responses) to establish a connection, configure security options (e.g., Internet Protocol Security), transmit and receive packets or frames via the connection, etc.

Moreover, as can be seen in FIG. 1, wireless signals 130 (represented by jagged lines) are transmitted by radios 128 in the components. For example, radio 128-1 in electronic device 110-1 may transmit information (such as packets) using wireless signals. These wireless signals may be received by radios 128 in one or more of the other components, such as by optional base station 112 or optional access point 116. This may allow electronic device 110-1 to communicate information to optional base station 112 or optional access point 116, and thus, to computer system 118.

In the described embodiments, processing a packet or frame in a component may include: receiving the wireless signals with the packet or frame; decoding/extracting the packet or frame from the received wireless signals to acquire the packet or frame; and processing the packet or frame to determine information, contained in the packet or frame (such as information for inclusion in the set of records 120, a request, a notification, etc.).

Note that the communication between at least any two of the components in system 100 may be characterized by one or more of a variety of performance metrics, such as: a received signal strength indication (RSSI), a data rate, a data rate for successful communication (which is sometimes referred, to as a 'throughput'), an error rate (such as a retry or resend rate), a mean-square error of equalized signals relative to an equalization target, intersymbol interference, multipath interference, a signal-to-noise ratio, a width of an eye pattern, a ratio of number of bytes successfully communicated during a time interval (such as 1-10 s) to an estimated maximum number of bytes that can be communicated in the time interval (the latter of which is sometimes referred to as the 'capacity' of a communication channel or link), and/or a ratio of an actual data rate to an estimated data rate (which is sometimes referred to as 'utilization').

Figure 14:
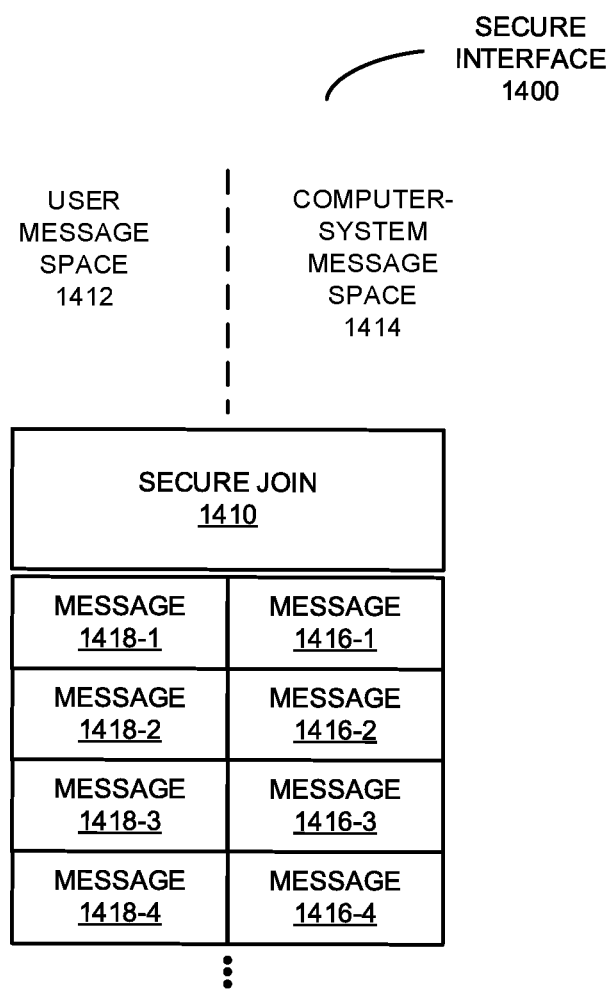
FIG. 14 is a drawing illustrating a secure interface for communicating information in the system in FIG. 1 in accordance with an embodiment of the present disclosure.

As discussed below with reference to FIG. 14, one or more users (such as an individual or a group of individuals) may use electronic device 110-1 to request, via network 126, access to information in one or more records in set of records 120. If the one or more users are authorized to access the one or more records, computer system 118 may securely and anonymously provide, via network 126, the requested information (or a pointer to the requested information) to electronic device 110-1 via a user interface. Furthermore, notification engine 124 may analyze the set of records 120 and may selectively provide, via network 126, notifications to one or more of electronic devices 110 and, thus, to the associated users of these electronic devices. For example, the notifications may include timely health messages that are securely and anonymously provided to at least a user via a user interface.

Moreover, as discussed further below with reference to FIGS. 8-13, information in the set of records 120 may be, at least in part, encrypted or securely hashed and stored separately from the encryption key(s) or the secure hashing function(s). For example, encrypted information and the associated public encryption keys may be stored in the set of records 120, and the corresponding private encryption keys may be stored separately.

Furthermore, as discussed further below with reference to FIGS. 2-7, one or more users may use one of electronic devices 110 (such as electronic device 110-1) to provide, via network 126, information to computer system 118 for inclusion in one or more records in set of records 120. In response to receiving this information, security engine 122 may securely store the information in the one or more records. In particular, security engine 122 may: scramble timestamps (and, more generally, words or values in a timeline); substitute replacement fields (such as random or pseudorandom alphanumeric information) for fields in set of records 120 (such as based on predefined substitution rules, the cardinality of the fields and, more generally, the information value of the fields), and/or generate artificial or fictitious records based on, at least in part the set of records 120 so that at least some of the phrases or values in the combination of the artificial records and the set of records 120 have uniform distributions or frequencies of occurrence. Note that security engine 122 may randomly or pseudo-randomly order the positions of the artificial records in the set of records 120.

In some embodiments, security engine 120 may 'detune' an invariant signature that describes or predicts the responses of voxels in a biological lifeform or organism (such as an animal or a human being) to a particular measurement technique based on measurement, imaging or scanning instructions, so that a reversible 'incorrect' response of the biological organism can be stored in the set of records 120. This approach may show security engine 120 to store large amounts of data (such as medical images or imaging data) without requiring that these fields in the set of records 120 be secured using an encryption technique (such as symmetric or asymmetric encryption, or a secure hashing function). Because medical images include very large amounts of data, this approach, therefore, may significantly reduce the processing time and the resources in computer system 118 that are needed to secure the set of records 120.

In these ways, security engine 122 may reduce or eliminate context or contextual information from the set of records 120 while maintaining the relevance or meaning of the information. This approach may allow the secured information in the set of records 120 to be accessed while preventing unauthorized access to meaningful information in the set of records 120.

Note that the measurement technique may include a wide variety of non-invasive measurement techniques, including; a magnetic-resonance (MR) technique, computed tomography, ultrasound imaging, x-ray imaging, positron emission spectroscopy, electron spin resonance, optical/infrared spectroscopy (e.g., to determine a complex index of refraction at one or more wavelengths), an electrical measurement (such as an electrocardiogram, an electromyogram, an electroencephalogram, etc.), proton beam, photoacoustic imaging, other non-destructive measurements (such as radar or millimeter-wave scanning), activity or behavior data for the biological organism (such as data capture using a wearable electronic device), measurements performed by nano particles in the biological organism, chemical composition of fluids (such as blood) measured at arbitrary locations in the biological organism non-destructively or by drawing a blood sample (e.g., using microfluidics), another quantitative or qualitative characteristic or property of the biological organism, etc.

Moreover, the quantitative analysis of MR scans in the measurement technique may be facilitated by the use of MR fingerprints of biological organism that are magnetic-field invariant (which are sometimes referred to as 'magnetic-field-invariant MR signatures' or 'invariant MR signatures'). The invariant MR signatures may describe the dynamic MR responses of voxels at 3D positions in the one or more biological organisms at arbitrary magnetic-field strengths. Moreover, the invariant MR signatures may be independent of the MR scanners, as well as the specific scanning instructions magnetic-field strengths and/or pulse sequences), used to acquire MR signals in a variation on MRF (which is sometimes referred to as 'quantitative MRF' or QMR-X) that were then used to determine the invariant MR signatures. An invariant MR signature may be determined by iteratively converging MR signals of one or more types of nuclei in a biological organism, which were acquired by an MR scanner based on scanning instructions, with simulated MR signals (which are sometimes referred to as calculated MR signals or estimated MR signals) for the biological organism that are generated using an MR model and the scanning instructions.

Furthermore, the measurement technique may be used in conjunction with a variety of MS techniques, including: magnetic-resonance imaging (MRI), magnetic-resonance spectroscopy (MRS), magnetic-resonance spectral imaging (MRSI), magnetic-resonance thermometry (MRT), magnetic-resonance elastography (MRE), MR fingerprinting (MRF), magnetic-field relaxometry, diffusion-tensor imaging and/or another MR technique (such as functional MRI, metabolic imaging, molecular imaging, blood-flow imaging, etc.). Note that these MR techniques are each a form of quantitative tensor-field mapping.

In particular, 'MRI' should be understood to include generating images (such as 2D slices) or maps of internal structure in a sample (such as anatomical structure in a biological sample, e.g., a tissue sample or a patient) based on the dynamic response of a type of nuclear spin (such protons or the isotope $^1$H) in the presence of a magnetic field, such as a non-uniform or spatially varying external magnetic field (e.g., an external magnetic field with a well-defined spatial gradient). Moreover, MRS should be understood to include determining chemical composition or morphology of a sample (such as a biological sample) based on the dynamic response of multiple types of nuclear spins (other than or in addition to $^1$H) in the presence of a magnetic field, such as a uniform external magnetic field.

Moreover, 'MRSI' should be understood to include generating images or maps of internal structure and/or chemical composition or morphology in a sample using MRS in the presence of a magnetic field, such as a non-uniform or spatially varying external magnetic field. For example, in MRSI the measured dynamic response of other nuclei in addition to $^1$H are often used to generate images of the chemical composition or the morphology of different types of tissue and the internal anatomy of the biological organism.

Furthermore, in contrast with existing approaches to MRI or MRSI that usually provide qualitative or 'weighted' measurements of a limited set of properties, 'MRF' should be understood to include quantitative measurements of the properties of a sample by acquiring signals representing a dynamic or time-dependent magnetization or MR trajectory from different materials in a sample using a pseudorandom pulse sequence. In particular, instead of using repeated, serial acquisition of data to characterize individual parameters that are of interest, in MRF signals from different materials or tissues are often acquired using a pseudorandom pulse sequence to determine a unique signal or 'fingerprint' (e.g., a time-dependent magnetization or MR trajectory). The resulting unique fingerprint of the sample is, in general, a function of multiple material properties under investigation. For example, MRF can provide high-quality quantitative maps of a spin-lattice relaxation time $T_1$ (which is the time constant associated with the loss of signal intensity as components of the nuclear-spin magnetization vector relax to be parallel with the direction of an external magnetic field), a spin-spin relaxation time $T_2$ (which is the time constant associated with broadening of the signal during relaxation of components of the nuclear-spin magnetization vector perpendicular to the direction of the external magnetic field), proton density (and, more generally, the densities of one or more type of nuclei) and diffusion (such as components in a diffusion tensor).

Note that 'magnetic-field relaxometry' (such as $B_0$ relaxometry with the addition of a magnetic-field sweep) may involve acquiring MR images at different magnetic-field strengths. These measurements may be performed on the fly or dynamically (as opposed to performing measurements at a particular magnetic-field strength and subsequently cycling hack to a nominal magnetic-field strength during readout, i.e., a quasi-static magnetic-field strength). For example, the measurements may be performed using un-tuned radio-frequency (RF) coils or a magnetometer so that measurements at the different magnetic-field strengths can be performed in significantly less time.

Additionally, 'MRE' should be understood to include measuring the stiffness of a sample using MRI by sending mechanical waves (such as sheer waves) through a sample, acquiring images of the propagation of the shear waves, and processing the images of the shear waves to produce a quantitative mapping of the sample stiffness (which are sometimes referred, to as 'elastograms') and/or mechanical properties (such as rigidity, density, tensile strength, etc.).

Moreover, 'MRT' should be understood to include measuring maps of temperature change to a sample using MRI.

Note that a biological organism may include a tissue sample from an animal or a person (i.e., a portion of the animal or the person). For example, the tissue sample may have been previously removed from the animal or the person. In some embodiments, the tissue sample is a pathology sample, such as a biopsy sample. Thus, the tissue sample may be formalin fixed-paraffin embedded. However, in other embodiments a biological organism may be in the animal or the person (i.e., an in-vivo sample) and/or the measurement technique involves whole-body scans. Furthermore, the measurement technique may also be applied to inanimate (i.e., non-biological) samples of a wide variety of different materials. In the discussion that follows, the biological organism is a person or an individual, which is used as an illustrative example. Moreover, while the measurement technique may be used with a wide variety of non-invasive measurement techniques, in the discussion that follows MR techniques, and in particular MRI and MRS, are used as illustrative examples.

Although we describe the network environment shown in FIG. 1 as an example, in alternative embodiments, different numbers or types of electronic devices may be present. For example, some embodiments comprise more or fewer components. As another example, in another embodiment, different components are transmitting and/or receiving packets or frames.

Figure 2:
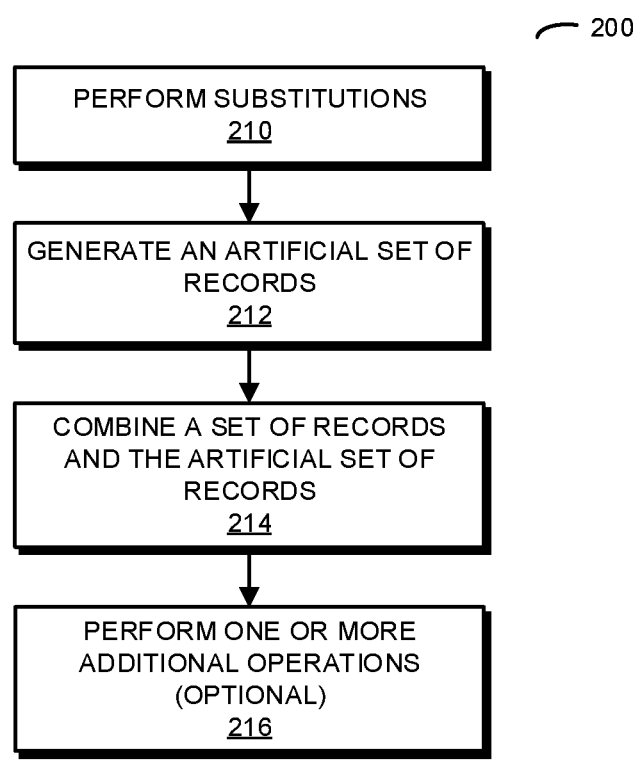
FIG. 2 is a flow diagram illustrating a method for securing a set of records using the system in FIG. 1 in accordance with an embodiment of the present disclosure.

FIG. 2 presents embodiments of a flow diagram illustrating method 200 for providing securing a set of records, which may be performed by a computer system (such as computer system 118 in FIG. 1). During operation, the computer system (such as a processor executing a program module and, more generally, software executed in an environment, e.g., an operating system, of the computer system) performs substitutions (operation 210) for fields in the set of records, where performing a given substitution involves replacing a field in the set of records (which may include one or more records) with a replacement field, and the substitutions remove context information in the set of records while maintaining relevance of the set of records. Note that the replacement field may include random or pseudorandom alphanumeric information. Furthermore, the substitutions may be predefined, such as based on predefined substitution rules (e.g., replace instances of a particular word or phrase with a corresponding substitution). Alternatively or additionally, the substitutions may be determined based on information value of the fields in the set of records. For example, the substitutions may be determined based on a cardinality of the fields in the set of records.

Then, the computer system may generate an artificial set of records (operation 212) based, at least in part, on the set of records, where a given artificial record includes one or more modified portions of the set of records.

Next, the computer system may combine the set of records and the artificial set of records (operation 214) into a second set of records, where at least some phrases or values in the second set of records are uniformly distributed. Note that the set of records and the artificial set of records may be randomly or pseudo-randomly ordered in the second set of records.

In some embodiments, the computer system performs one or more optional additional operations (operation 216). For example, the computer system may reorder fields that include timestamps in the set of records. These fields may include one or more words or second values (which may be the same or different from values in the fields that were replaced during the substitution in operation 210). Alternatively or additionally, the computer system may modify imaging data in the set of records based on imaging instructions and an invariant signature that predicts responses of voxels in at least an individual.

In some embodiments of method 200, there may be additional or fewer operations. Moreover, the order of the operations may be changed, and/or two or more operations may be combined into a single operation.

Figure 3:
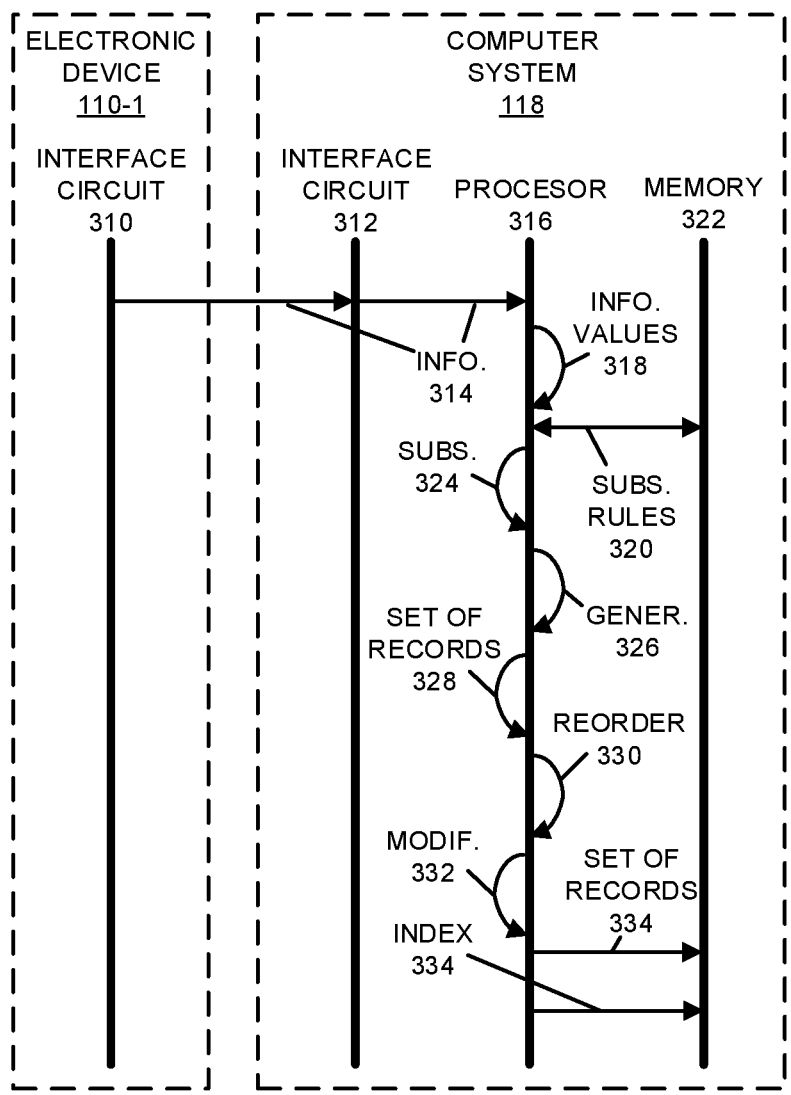
FIG. 3 is a drawing illustrating communication among components in the system, in FIG. 1 in accordance with an embodiment of the present disclosure.

Embodiments of the security technique are further illustrated in FIG. 3, which presents a drawing illustrating communication among components in system 100 (FIG. 1). In particular, during the security technique, interface circuit 312 in computer system 118 may receive information 314 corresponding to the set of records from interface circuit 310 in electronic device 110-1. This information 314 may be provided to processor 316.

After receiving information 314, processor 316 may secure information 314. In particular, processor 314 may perform substitutions 324 for fields in the set of records. These substitutions may be based on predefined substitution rules 320 access by processor 316 in memory 322. Alternatively or additionally, processor 314 may analyze information 314 to calculate information values 318 of the fields, and substitutions 324 may be based on the information values 318.

Moreover, processor 310 may generate 326 an artificial set of records based, at least in part, on the set of records, and may combine the set of records and the artificial set of records (operation 214) into a second set of records 328.

Furthermore, processor 316 may reorder 330 fields that include timestamps in the set of records and/or may modify 332 imaging data in the set of records based on imaging instructions and an invariant signature that predicts responses of voxels in at least an individual (and, more generally, a biological organism).

Then, processor 316 may store the result set of records 334 in memory 322. In some embodiments, set of records 334 are appended to existing records in memory 322, so that no previously stored information is lost or modified.

In addition, processor 316 may store an index 336 that can be used to reverse the operations used to secure information 314 so that information 314 can be recovered in set of records 334.

In this way, the computer system may secure the information in the set of records, such that, even in the event of a security breach (in which the set of records are accessed or stolen by an unauthorized user), the information may be secure. For example, the reversible substitutions and obfuscation of the information in the set of records may remove the context to prevent an unauthorized viewer from extracting meaningful information from the set of records. In addition, the modifications may include reordering that facilitates increased compression of the set of records. However, the modifications to the set of records may preserve relevance (such as fields associated with a particular biological organism and/or a particular transaction, e.g., a doctor's appointment), so the changes to the set of records can be reversed and so the information in the set of records can be identified and accessed. Consequently, the security technique may enhance the safety of the information in the set of records while preserving its usefulness. Therefore, the security technique may improve compliance with regulatory requirements (such as HIPAA), which may increase user trust and satisfaction.

In an exemplary embodiment, the security technique is used to secure a set of records, such as medical records. In particular, a set of medical records may include individual patient transactions (office visits, lab results, etc.) with associated timestamps. In addition, the set of medical records may include metadata for one or more patients. This metadata may be included in separate records or may be integrated into the transactional information. For example, the metadata may include a location where services were provided.

The information in the set of medical records can be used to directly identify a patient, at least in an abstract way. For example, the set of medical records may include a patient identifier (such as a numerical value).

However, the content of the information in the set of medical records and the relationship between different fields in the set of medical records (which collectively are sometimes referred to as 'context') can be used to specifically identify the patient. For example, if a patient has a particular rare disease and they receive services from a specific physician at location in city (such as San Francisco), this information can be used to determine the identity of the patient. In particular, the information can be used in conjunction with social-media posts, zip codes, travel records, public records, newspaper articles, calendars, known relatives, doctor, and/or other relevant information to uniquely determine the identity of the pattern, thereby constituting a breach of HIPAA regulations and the patient's privacy and trust.

Figure 4:
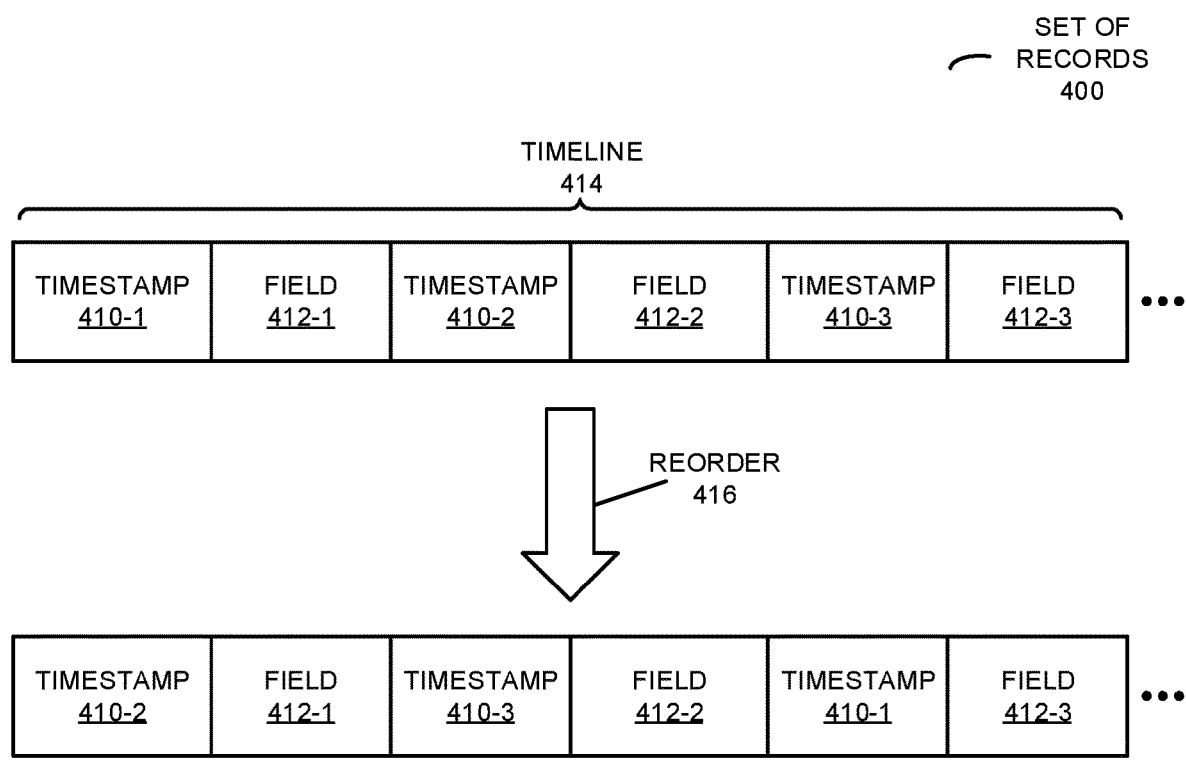
FIG. 4 is a drawing illustrating securing a set of records in the system in FIG. 1 in accordance with an embodiment of the present disclosure.

In order to prevent this from happening while maintaining the usefulness of the set of medical records, the security technique may remove the contextual information from the set of medical records while maintaining the relevance or meaning of the information in the set of medical records. For example, as shown in FIG. 4 presents a drawing illustrating securing a set of records 400 in system 100 (FIG. 1), fields 412 with timestamps 410 in a timeline 414 may be scrambled or reordered 416. In some embodiments, scrambling or reordering timestamps 412 involves replacing timestamps 410 with random or pseudorandom values.

Figure 5:
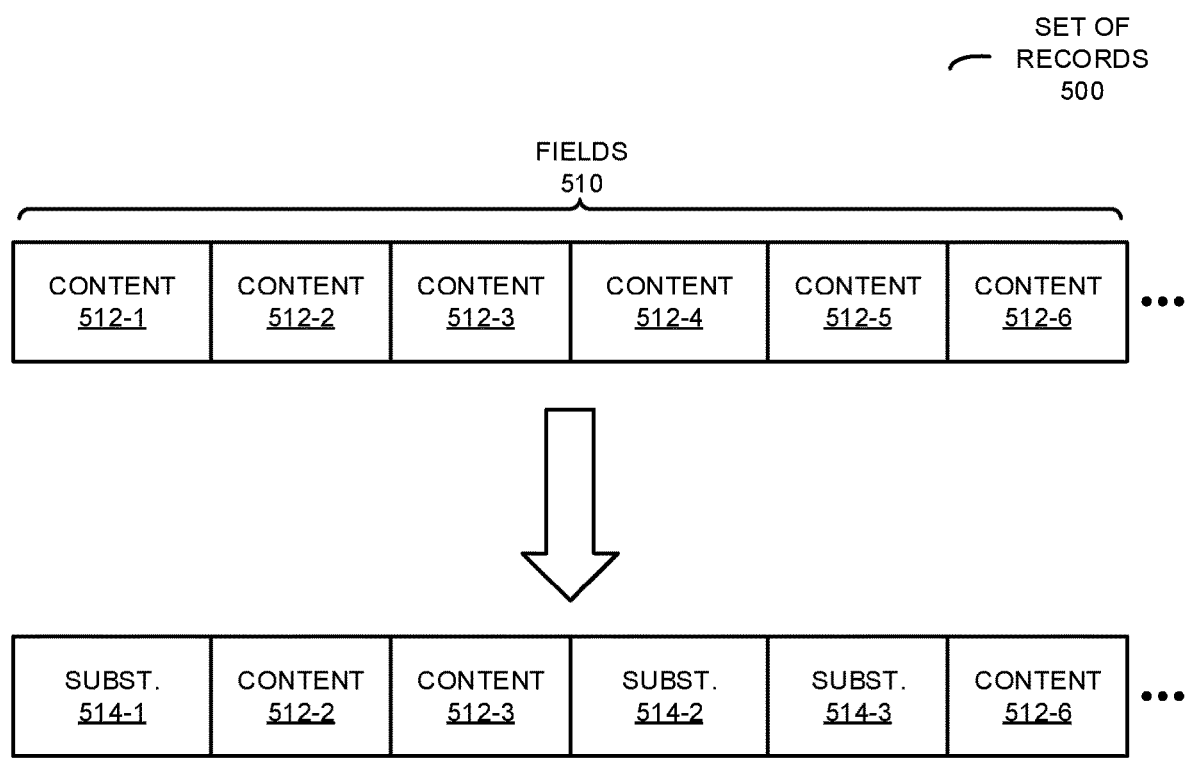
FIG. 5 is a drawing illustrating securing a set of records in the system, in FIG. 1 in accordance with an embodiment of the present disclosure.

Moreover, the security technique may include at least selective information hiding. In particular, constant substitutions may be performed over the set of medical records, such that a particular word or phrase (e.g., San Francisco) is replaced by a corresponding random or pseudorandom alphanumerical value ('A7cU3lz'). However, other information, such as the patient identifier, may not be substituted. The substitutions are illustrated in FIG. 5, which presents a drawing illustrating securing a set of records 500 in system 100 (FIG. 1). In particular, content 512 (such as words, phrases and/or values) in at least some of fields 510 is replaced by substitutions 514.

In some embodiments, at least some of the content in fields 510 in the set of medical records are substituted or replaced. In particular, by not performing substitutions for all the words, phrases and values in the set of medical records, a smaller state of substitutions needs to be tracked in a look-up table for use when reversing the substitutions (as well as the reordering and/or the obfuscating). For example, the substitutions may be prioritized based on the information value of fields 510. In some embodiments, the substitutions are based on the cardinality of the content in fields 510, such that fields with higher cardinality (e.g., three or more values, which is used as an illustration and is not intended to be limiting) are replaced. Alternatively or additionally, the substitutions may be based on the frequency of occurrence in the set of medical records and/or the usefulness of the content in determining the identity of the patient.

Furthermore, because the frequency of occurrence of content in the set of medical records can be used to determine the relative importance of information and, thus, to identify the patient, the security technique may include generating an artificial or fictitious set of medical records based the set of medical records (such as based on the initial frequencies of occurrence of words, phrases and/or values in at least some of the fields). This is shown in FIG. 6, which presents a drawing illustrating securing a set of records 600 in system 100 (FIG. 1), including real medical records 610 and artificial medical records 612.

Note that the artificial set of medical records may incorporate at least portions of the set of medical records. Moreover, the artificial set of medical records may be randomly or pseudorandomly combined with the set of medical records (e.g., in random order) such that the final frequencies of occurrence or distributions of the words, phrases and/or values in at least some of the fields is uniform or flat (or another distribution, such as a normal distribution). Therefore, the stored medical records may include real and fake longitudinal health records. Furthermore, note that this approach may be applied to the medical data as well as the associated metadata in the set of medical records.

As noted previously, the changes applied to the set of medical records or information that can be used to reverse the changes may be stored in an index or a look-up table that is associated with the patient identifier, so that, as needed, the original information in the set of medical records can be restored. Note that the index or look-up table may be stored separately from the set of medical records and may be separately secured (e.g., using a secure hashing function, encryption, etc.).

As described previously, in some embodiments the computer system uses a predetermined invariant signature and measurement instructions to intentionally generate incorrect data (such as imaging data) that is scored in the set of records (e.g., in a separate location in memory from the invariant signature and the measurement instructions). This may allow large amounts of data to be stored without requiring the use of encryption. Moreover, the errors included in the incorrect data may be subsequently reversed when a request to access the data is received. For example, an integral equation (such as a convolution or a correlation integral equation) may be used to calculate the correct data based on a generating function (such as a Green's function). This approach may allow a computationally efficient pipeline to restore the correct data, which can then be provided to the user that requested it.

As so illustration, we now describe an invariant signature for MR (which is referred to as an 'invariant MR signature'). The invariant MR signature may be based on an MR model of the dynamic response of voxels in a biological organism to an external magnetic field and measurement conditions that are described or specified in scanning instructions (e.g., magnetic-field strengths, pulse sequences, the voxel size, one or more spectra, one or more types of nuclei, etc.). Stated differently, the MR model may accurately predict MR signal evolution or response for the voxels in the biological organism over a range of parameters ($T_1$, $T_2$, proton density, off-resonances, environment, location, temperature, pulse sequences, etc.) using the Bloch equations, full Liouvillian computations or another simulation techniques.

Using the Bloch equations as an illustrative example, the MR model may be a 3D model of voxels in a portion of a biological organism (and, more generally, a biological organism), and may include parameters in the Bloch equations for each of the voxels. In particular, with a quasi-static magnetic field $B_0$ along the z axis, the Bloch equations are $$\frac{dM_x(t)}{dt} = \gamma \cdot \left(\vec{M}(t) \otimes \vec{B}(t)\right)_x - \frac{M_x(t)}{T_2},$$

$$\frac{dM_y(t)}{dt} = \gamma \cdot \left(\vec{M}(t) \otimes \vec{B}(t)\right)_y - \frac{M_y(t)}{T_2}, \text{ and}$$

$$\frac{dM_z(t)}{dt} = \gamma \cdot \left(\vec{M}(t) \otimes \vec{B}(t)\right)_z - \frac{M_z(t) - M_0}{T_1},$$

where $\gamma$ is the gyromagnetic ratio, $\otimes$ denotes a vector cross product and $\vec{B}(t) = (B_x(t), B_y(t), B_0 + \times B_x(t))$ is the magnetic field experienced by a type of nuclei in the biological organism. The parameters in the Bloch equations may include $T_1$, $T_2$, a density of a type of nuclei, diffusion, velocity/flow, temperature, and magnetic susceptibility. Note that there may be different parameters for different types of nuclei for each of the voxels. Moreover, note that the Bloch equations are a semi-classical, macroscopic approximation to the dynamic response of the magnetic moments of the type of nuclei in the biological organism to a time-varying magnetic field. For example, there may be 67 M cells in a 1 mm³ voxel.

By performing multiple measurements under different conditions, the underdetermined solution space for the parameters in the Bloch equations for the biological organism may be constrained and solved. For example, if a portion of the biological organism included one voxel, there may be 4-10 MR model parameters (which specify an invariant MR signature) that need to be determined for a particular type of tissue. If the voxel includes M types of tissue, there may be 4M-10M MR model parameters (which specify M invariant MR signatures) that need to be determined for the particular type of tissue. As the number of voxels increases, this can appear to be a daunting problem.

However, because different types of nuclei have different Larmor frequencies, the spatial distribution of the types of nuclei and their local concentrations may be determined from the measured MR signals. Then, a predefined anatomical template for the biological organism (or a portion of the biological organism), with associated initial parameters for an MR model, may be scaled to match the spatial distribution of the types of nuclei and their local concentrations.

Next, for a type of tissue (such as a particular organ), the MR model parameters may be iteratively refined as the size of the voxels is progressively decreased (and, thus, the number of voxels is increased). This analysis may be driven by the error between the measured MR signals and simulated MR signals using the MR model. Over time, the focus during the training will be on the residual regions with errors that are larger than a convergence criterion. For example, the parameters in the MR model may be trained based on measured MR signals at one magnetic-field strength and then the error may be determined or estimated based on the predictions of the MR model, at another magnetic-field strength. Furthermore, note that initially the MR model may assume that there is no contribution or interaction between different voxels. However, as the error and the voxel size is reduced, subsequently such contributions and/or interactions may be included when training the MR model.

In order to facilitate this fitting or computational approach, the measurement technique may determine 'surface signatures,' as opposed to 1D signatures. For example, using measurements at multiple magnetic-field strengths or in the presence of known magnetic-field disturbances (such as rotation), a set of MR trajectories may be determined as 'fingerprints' that can be used to determine the invariant MR signature(s). Note that each MR trajectory may be defined by a magnetic-field function rather than a fixed magnetic-field strength.

In an exemplary embodiment, a simulation that is used to determine the MR model may be vertex/voxel centric. Using a physical model (such as a Bloch-equation-based model) running at each vertex, the system may 'apply' pulse sequences or disturbance to the physical model of the biological organism being scanned. For example, a message may be broadcast to the vertices that describe the disturbance in terms of physical laws. Each of the vertices may compute its predicted change in state and the resulting forces and energies, which are then relayed as messages to adjacent vertices about the forces and energies exported from that vertex. When all the vertices have generated a message, the message has been forwarded to the adjacent vertices and the state of the system has been updated, a time interval in the calculation may be complete. This approach can be generalized so that the message is forwarded to non-cyclical paths of length N (where N is an integer) radiating out from the vertex to improve the accuracy of the simulation.

Once the state has been updated, a computational technique can be run over the new computed state and then compared to the measured state. The error may be the difference between the predicted state and the measured state. As the computational technique is applied, the system may determine how to optimally assign the current state to each vertex in a way that reduces or minimizes the global error. Next, the system may choose a new set of perturbations for the system and may broadcast these as a new message to the vertices, as well as executing this disturbance physically on the biological organism being scanned. In this way, the system may provide real-time or near-real-time analysis and feedback during the measurement technique.

Thus, the inverse problem of determining the MR model parameters based on measured MR signals may be 'solved' by minimizing the error or difference between the measured MR signals and simulated MR signals that are generated based on the MR model, characteristics of an MR scanner (such as magnetic-field inhomogeneity) and the scanning instructions used to acquire the measured MR signals. In some embodiments, the inverse problem is solved using one or more computational techniques, including: a least-squares technique, a convex quadratic minimization technique, a steepest descents technique, a quasi-Newton technique, a simplex technique, a Levenberg-Marquardt technique, simulated annealing, a genetic technique, a graph-based technique, another optimization technique and/or Kalman filtering (or linear quadratic estimation).

Note that the inverse problem may be solved using dynamic programming. In particular, the problem may be divided up and performed by multiple computers in parallel, e.g., in a cloud-based computing system. For example, a particular thread may attempt to solve the inverse problem for particular scanning instructions. Multiple potential parameter solutions generated by the computers (or processors) may be combined (e.g., using linear superposition) to determine an error metric that is minimized using the one or more computational techniques.

Moreover, the inverse problem may be solved Iteratively by first attempting to find suitable parameters (e.g., parameters that minimize the error between the MR signals and simulated MR signals) for the MR model using a coarse voxel size and then progressively finding suitable parameters with smaller voxel sizes. Note that the final voxel size used in this iterative procedure may be determined based on the gyromagnetic ratio of a type of nuclei being scanned. Furthermore, the voxel size or locations may also be chosen so that a voxel is evenly portioned into a set of subvoxels, or so that there is certain amount of overlap with preview voxel sizes to effectively 'oversample; the overlapping region and potentially further localize where an MR signal originates. This last technique may be akin to shifting the entire gradient system in one or more dimensions by a distance dx that is less than a characteristic length of the voxels (such as a length, a width or a height of the voxels). In some embodiments, the voxel size in the MR model is smaller than that used in the MR scans (i.e., the MR model may use a super-resolution technique).

Additionally, the MR model may include simulations of dynamics, such as motion associated with: respiration, a heartbeat, blood flow, mechanical motion, etc. (Thus, there may be additional terms in the Bloch equations for diffusion, thermometry, spectroscopy, elastography, etc. Consequently, the MR model may be based on the Bloch-Torrey equations, etc.) For example, when a voxel contains a space that has a fluid flowing through it (such as in a vein), the flow of the liquid may be simulated by building a map of the flow directions and velocity magnitudes in the biological organism being scanned to be accounted for it the computation of the invariant MR signature. Furthermore, when scanning a human or an animal, the MR model may include the resting motion (such as that associated with respiration, a heartbeat, etc.). In order to facilitate calculation of the MR model, measured MR signals and/or other temporal measurements may be synchronized with or relative to a reference clock or a biological time period.

The MR model may be used to predict bow the biological organisms will respond to particular scanning instructions. In particular, the MR model may be used to simulate or estimate the MR signals for a particular MR scanner having particular characteristics, for particular scanning instructions and/or for a particular biological organism (which may have a medical history, previous MR scan results, patterns of breathing, patterns of movement, etc.) Stated different, an invariant MR signature (which is based on the MR model) may be used to determine representations or projections (i.e., the MR signals) in particular contexts, such as based on the particular characteristics of the MR scanner, the particular scanning instructions and/or the particular biological organism.

Thus, the MR model may be determined using active learning. In particular, the MR model may be iteratively fit or determined based on 'queries' generated by a learning system or a learning engine (which may be implemented in computer system 114 in FIG. 1). The queries generated by the learning engine may include different magnetic-field strengths $B_0$, different electromagnetic pulse sequences and/or different ultrasonic pulse sequences that are based on confidence intervals for parameters in the MR model. Consequently, the learning engine may use the measured MR signals in response to these queries to determine unknown parameters in the MR model and/or parameters having a poor accuracy (such as a confidence interval greater than 0.1, 1, 5 or 10%). More generally, the adaptive learning may be based on a wide variety of measurements, such as optical/infrared spectroscopy, x-ray, computed tomography, proton beam, photoacoustic, ultrasound, etc.

While the preceding discussion used the Bloch equations as an illustrative example, in other embodiments full Liouvillian computations (such as a Liouville supermatrix of interactions between two or more elements) or another simulation technique are used. Note that the MR signals computed or predicted using the MR model may be sampled at a rate equal to or higher than twice the Nyquist frequency of MR signals acquired during an MR scan.

Figure 7:
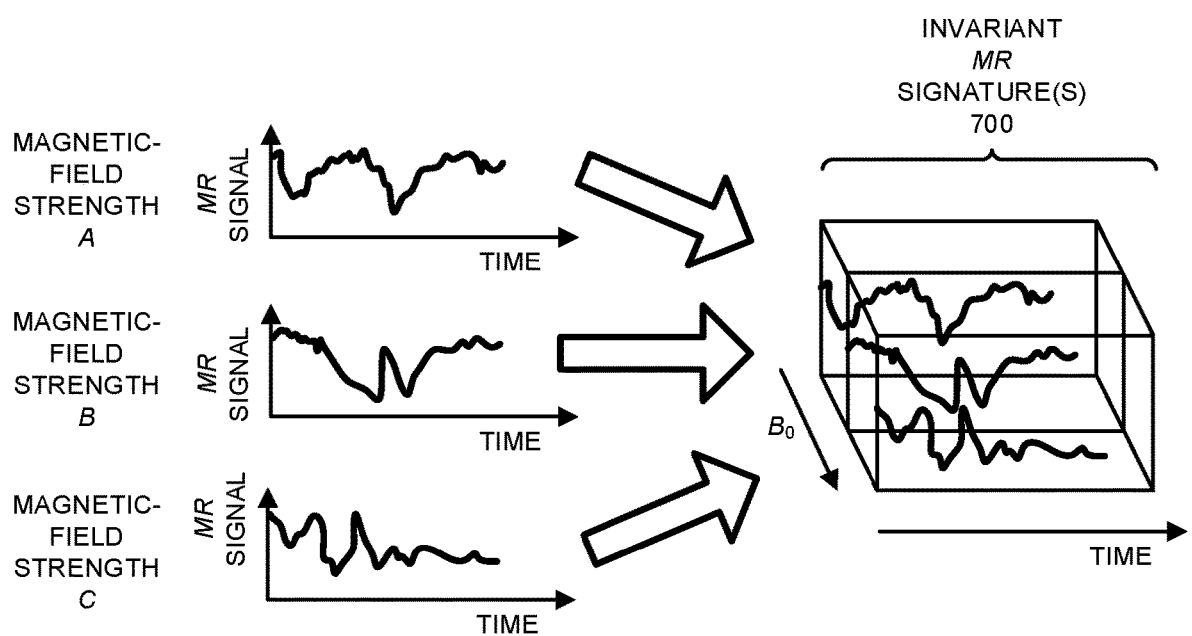
FIG. 7 is a drawing illustrating an invariant magnetic-resonance (MR) signature that specifies the response to a surface of magnetic-field strengths in accordance with an embodiment of the present disclosure.

FIG. 7, which presents a drawing illustrating an invariant MR signature that specifies the response to a surface of magnetic-field strengths, summarizes the preceding discussion of determining parameters for one or more MR models that accurately predict MR signals and their use in the biovault. In particular, MR signals or trajectories acquired at different magnetic-field strengths may be combined into a set of MR signals that specify the response to the surface of magnetic-field strengths. This response may be used to determine one or more invariant MR signatures 700.

Once the invariant MR signature(s) are known, they can be used to reversibly obscure MR signals or data that are stored in the set of records. For example, a systematic offset can be intentionally introduced into an invariant MS signature to detune the invariant MR signature and, thus, to generate incorrect data for the biological organism. The impact of this offset can be subsequently removed from the incorrect data using a generating function that is convolved with the incorrect data, thereby restoring the correct MR signals or data.

In addition to securing the set of records, the identities of users (such as patients), physicians or healthcare providers, etc., who access the set of records in the computer system and/or who receive notifications from the computer system based on the set of records may also be protected by anonymizing (and, thus, eliminating) edges or traceable communication paths during such communication. This approach may further protect the identities of users of system 100 (FIG. 1). While many of the preceding embodiments avoided the use of encryption, in general the following embodiments leverage encryption and/or secure hashing to secure the set of records and to protect the identifies of the users. We now describe these embodiments.

As more medical information becomes digitized, the need for secure storage of the medical information is becoming more important. While patients may want to enable researchers to use their data, they are often prevented from doing, so by fears about security and anonymity. Moreover, other users may not be comfortable with their data being included in any databases because they do not trust institutions with their data. While the embodiments of the security technique that are described below are illustrated in the context of healthcare, this approach can be used is a wide variety of industries where data needs to be securely shared with trusted advisors and/or opened up for anonymized research, while allowing a user to have full control over access to their identity information. For example, the security technique may be used in personal finance (e.g., a financial advisor may have access to a financial account, as can the compliance department in a financial institution, but the identity of the user can be maintained anonymously).

The security technique may facilitate improved security for users by separately storing identity information and sensitive data, thereby giving the users control over their data, while selectively allowing trusted access and general anonymized access to other trusted parties or advisors (such as a physician). Moreover, the security technique may also include secure messaging between, users (e.g., between a patient and a doctor, an account holder and a financial advisor, etc.), secure notices or notifications (e.g., a notice associated with a medical record that is automatically generated and that can only be read by a patient), secure access logs (e.g., any doctor or researcher that accesses the data of a patient may have their access logged, and the access log may be stored securely and may only be viewable by the patient or an authorized user), and/or connecting users creating a connection between a user and their doctor, which can enable the user to securely share information with their doctor in the future).

In some embodiments, at least some of the data and user information in the set of medical records, as well as associated communications, are stored in a manner that is not directly accessible to the computer system. In particular, at least some of the information in the set of medical records may be encrypted and/or securely hashed, and the encryption key and the secure bashing function (such as SHA-256) may be stored separately from the encrypted information or may be encrypted using different encryption keys from the one or more encryption keys that were used to encrypt the information. In some embodiments, the encrypted information is stored in the set of records along with the associated public encryption key, and the corresponding private encryption key is stored separately.

Figure 8:
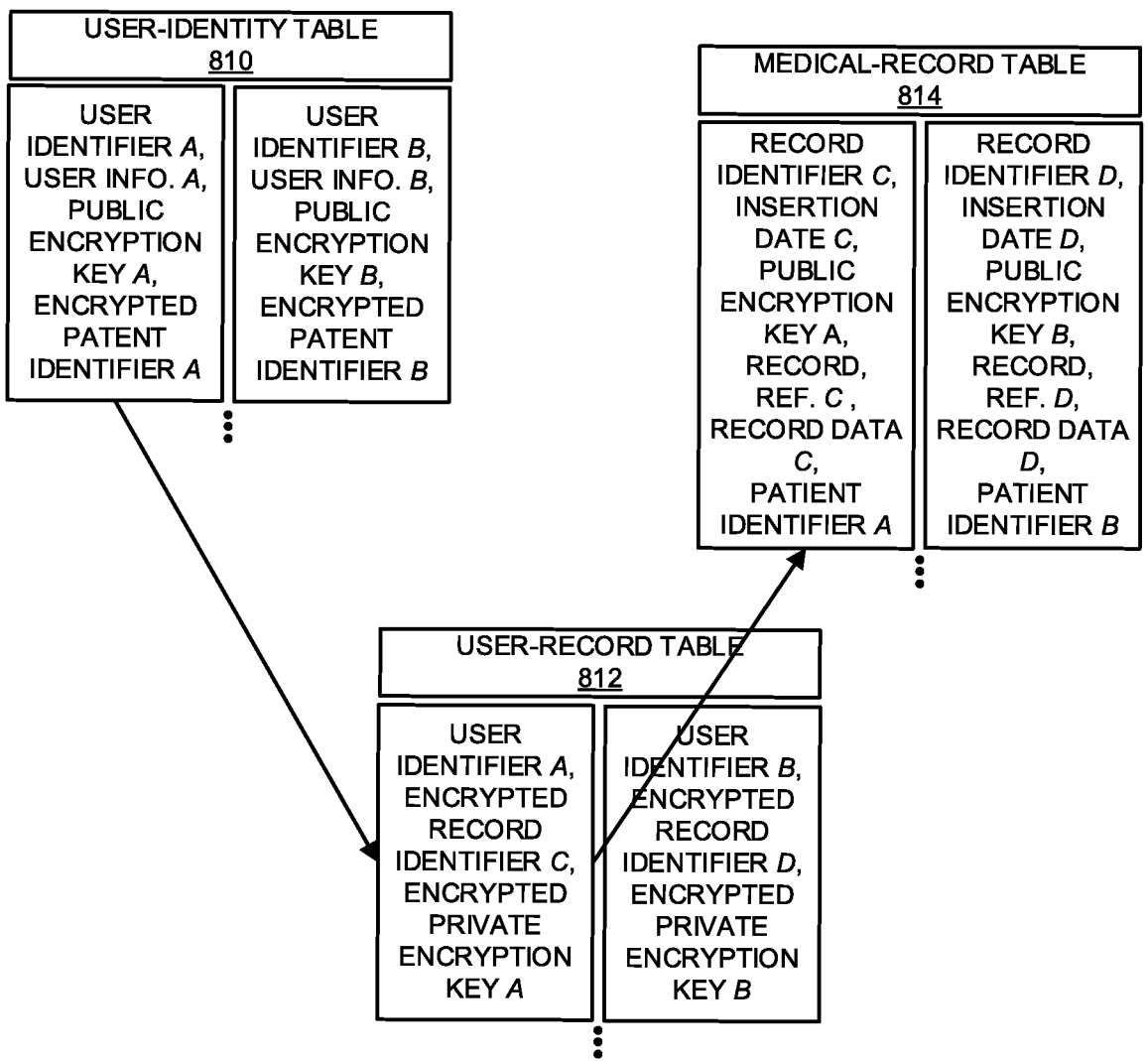
FIG. 8 is a drawing illustrating secure storage of a set of records in the system in FIG. 1 in accordance with an embodiment of the present disclosure.

As shown in FIG. 8, which presents a drawing illustrating secure storage of a set of records, the set of records may include encrypted and unencrypted information. In particular, secure data structure 800 may include a user-identity table 810, a user-record table 812, and a medical-record table 814. The user-record table 812 may provide a link between the user identity entries stored in the user-identity table 810 and record entries the medical-record table 814, and the information in the user-record table 812 may be encrypted such that the identity information entries stored in the user-identity table 810 may be securely separated from the medical record information stored in the medical-record table 814. Note that the tables may all be included in the same data structure (such as a text file, a string, a database, etc.), they can be stored in separate data structures, and/or the tables can be stored in a distributed system, such as a cloud-computing system.

The user-identity table 810 may include one or more user-identity entries. The user-identity entries can include identifying information about a user (e.g., a patient, a doctor, an animal, an organization or institution, etc.). For example, user-identity table 810 may include: a user identifier, user information (such as a name of the user, a birthdate of the user, credentials of the user, a photograph of the user, a list of relatives of the user), a public encryption key of a public encryption key-private encryption key pair associated with the user and/or an encrypted patient identifier (which is described further below). The corresponding private encryption key can be stored in user-record table 812 as a token or may be encrypted using a password or a biometric identifier that is associated with the user (such as a fingerprint or a retina scan) and that is carried on their person or in a personal device (such as a portable computing device or smartphone).

In some embodiments, the entries in the user-identity table 810 can include an encrypted patient identifier (which may be different from the user identifier), and the patient identifier may be encrypted using the public encryption key of the public encryption key-private encryption key pair associated with the user. The public encryption key-private encryption key pair associated with the user may be generated or created when a user is first created in the computer system, and multiple public encryption key-private encryption key pairs can be used by a single user (e.g., so that the user may have redundant encryption-key access in case a token containing a private encryption key is lost, discarded or compromised). Note that the encrypted patient identifier can be decrypted using the private encryption key of the public encryption key-private encryption key pair associated with the user. If stored in the user-identity table 810, the patient identifier may be encrypted using the user's public encryption key, and can be decrypted using the user's private encryption key, which may facilitate faster look-ups of medical records.

Moreover, the medical-record table 814 may include one or more medical-record entries, be it a single datum (such as a patient weight) to a full quantitative MR scan. Medical-record entries may be created in the presence of an account holder, and these medical-record entries are sometimes referred to as 'root records.' A root record that does not reference any other records. For example, a common root record is a record of a patient visit. Note that each medical record may have an associated public encryption key-private encryption key pair. The public encryption key for a medical record may be stored with the medical record. The corresponding private encryption key associated with the medical record may be encrypted and stored in a look-up table, such as user-record table 812. Note that when a patient signs into the computer system or provides their login credentials (e.g., using their cellular telephone), the computer system may create a visit record and may insert the record identifier and private encryption key into the look-up table (such as the user-record table 812).

The public encryption key of the public encryption key-private encryption key pair associated with each medical record can be used to test the authenticity of attempts to access the medical records via access tokens. Moreover, the other records inserted based on a patient's visit can referenced using a visit record identifier. Therefore, at no other point during the patient's visit does the patient identity have to be accessed.

Additionally, each medical record entry in the medical-record table 814 may include a visit identifier in order to record information captured daring the same visit to a medical facility (e.g., a blood test, an x-ray, an MRI, a urine sample, a hydration measurement, blood pressure, images of the ears, nose, throat, skin and body temperature, etc.).

The 'record references' may include one or more record that the record is in reference to or linked to, such as derivative medical records. For example, derivative medical records or record references may include a medical history update record that points to the patients visit (root) record or a model for analysis that is derived from raw scan data, for example, a difference between, two or more medical (root) records (e.g., a comparison of blood pressure between two visits). Additional medical records can include raw data (including timestamps, MRS capture parameters and signals, MR fingerprinting parameters and signals, etc.) and metadata (such as data generated from or in response to the MR data). The current height and or historical height measurements, current weight and or historical weight measurements, current blood pressure and or historical blood pressure, a medical history, a family medical history, genome sequencing done on the individual and/or their family (or a subset of their family), current symptoms, previous medical images, previous blood work, previous microbiome work, previous urine and/or stool analysis, temperature measurement or thermal imaging readings, optical pictures of the patient (including, but not limited to, eyes, ears, throat, nose, etc.), body-impedance measurements, measurements pertaining to a subjects hydration level or diet, previous surgeries, hospital stays, medical laboratory test results (such as biopsies), treatments, medications currently being taken, allergies, etc. In particular, the raw MR data can include, but is not limited to: raw MR signal data, raw capture timestamps, and metadata, which can include, but is not limited to, optional segmentation data, study logs, optional anomaly detection results (which, for a voxel, may include membership in one or more anomalies), optional radiologist identifications, and/or optional registration alignments (which can help in registering images faster using point-set registration or any other registration technique).

In some embodiments, meta information or metadata stored in entries in the medical-record table 814 may include: a record identifier to identify each unique medical record in the medical-record table 814, an insertion/creation date to indicate when the record was created or added to the table, and/or a pattern identifier. The patient identifier can enable querying of medical records in the medical-record table 814 by the patient, for example, in order to view the changes in medical records of a patient over time, etc.

Note that user-record table 810 may be a look-up table that associates the user with their records. At least a portion of the body of this record may be encrypted so that it is only accessible in the presence of the user's private encryption key. More specifically, the user-record table 812 can include entries containing unencrypted user identifiers, and also can include an encrypted body of encrypted medical-record or record identifiers, and encrypted private encryption keys associated with the public encryption key-private encryption key pair associated with each medical record, both of which may be encrypted using the public encryption key associated with the user identifier. (Note that the body of each entry in the user-record table 812 can be encrypted when the user records are created.) The user-record table 812 may provide a link between the user identity entries stored In the user-identity table 810 and record entries the medical-record table 814 and, because at least a portion of the information is encrypted, the identity-information entries stored in the user-identity table 810 may be stored securely and separately from the medical-record information stored in the medical-record table 814. As noted previously, at least portions of each entry in the user-record table 812 may be encrypted using the user's public encryption key (and can be decrypted using user's private encryption key), and each user record in the user-record table 812 may contain the encrypted medical-record identifier, and the encrypted private encryption key that proves ownership of the medical record, which can be verified using the public encryption key that is stored with the medical record. (Thus, each medical record may include a public encryption key-private encryption key pair associated with the record, and the public encryption key may be stored alongside or with the record.) Moreover, for each user identifier, the record identifier and the private encryption key of the public encryption key-private encryption key pair associated with each medical record may be encrypted with the user's private encryption key, so there is no way to associate the identity with medical record without the user's private encryption key.

Figure 9:
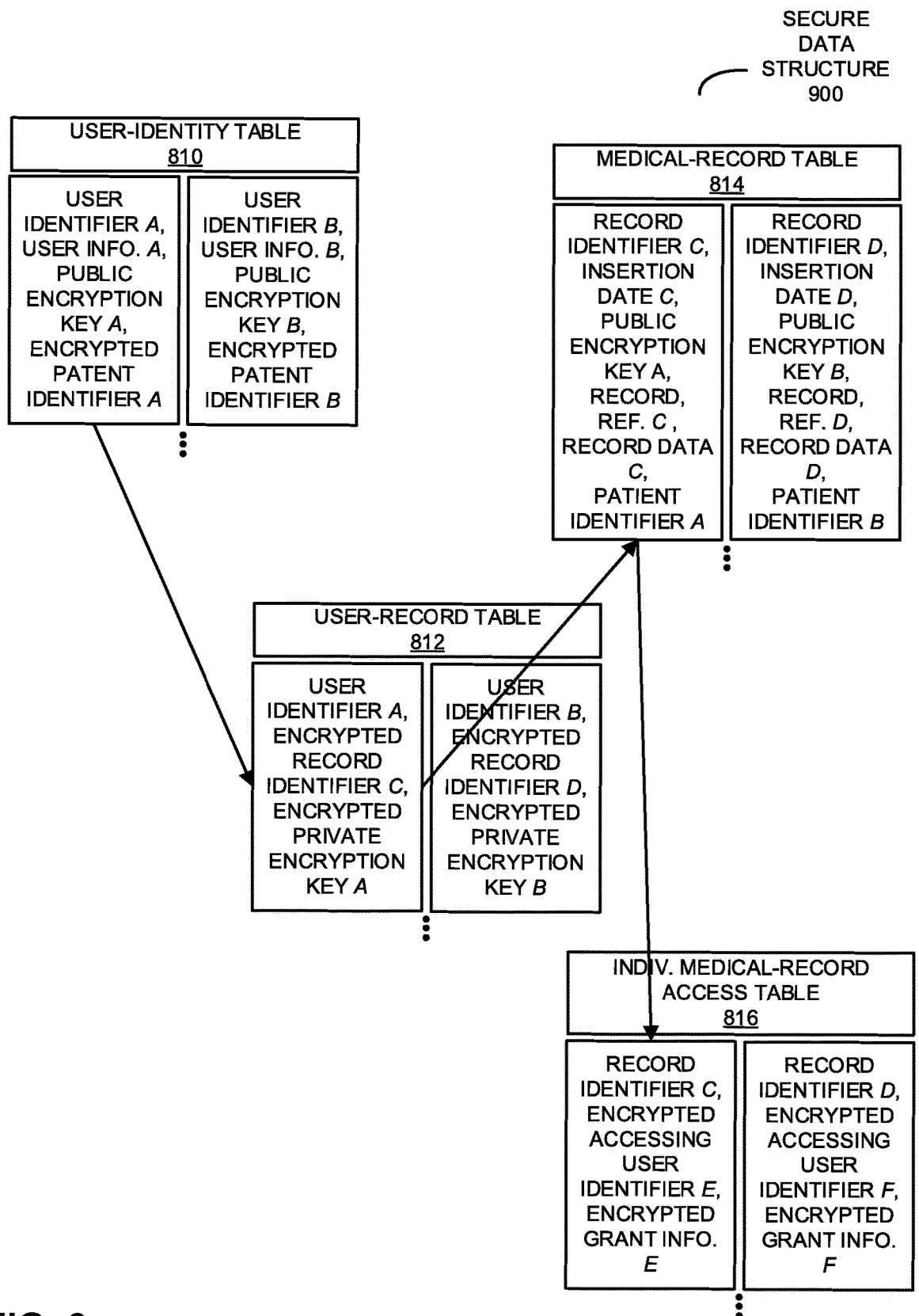
FIG. 9 is a drawing illustrating secure storage of a set of records in the system in FIG. 1 in accordance with an embodiment of the present disclosure.

As shown in FIG. 9, which presents a drawing illustrating secure storage of a set of records, secure data structure 900 may include user-identity table 810, user-record table 812, medical-record table 814, and an individual-medical-record access table 816. The individual-medical-record access table 816 may create a new log entry in the individual-medical-record access table 816 every time a medical record/root record is accessed, and the access log entry may be encrypted with the public encryption key associated with the medical record being accessed. For example, a patient may access their own medical history to review their historical blood pressure. Alternatively or additionally, their family doctor may review their records as requested by the patient. To the extent that, a user or a patient allows researchers access to the data (either anonymously or non-anonymously), the patient can track any researchers or other accesses to their medical records, and possibly information about that request such as the data accessed, when, by whom and for what purpose.

The goal in these embodiments of the security technique is to keep or to maintain access records in the form of an auditable access log. However, such access logs could compromise the other anonymization efforts in the security technique if it is not properly designed. In order to address this challenge, when a record is accessed, the access information may be stored encrypted against the public encryption key assigned to the medical record. In this way, the owner of the medical record can view (or export) the access history data, but it cannot be accessed by the computer system or a third party, and it also cannot be tampered with or spoofed. Any access by way of a token should also include any grant information (but not the signature, so the token cannot be re-used), as will be described further below. Note, therefore, that the grant information may be included in or specified by the token.

Medical record access logs can be decrypted using the private encryption key associated with the medical record because each user record may contain the encrypted medical-record identifier, and the encrypted private encryption key may be used to generate/sign an access token (as will be described below with reference to FIG. 11) for a user identifier. Afterwards, for each user identifier, the record identifier and the private encryption key of the public encryption key-private encryption key pair associated with the record may be encrypted using the user private encryption key, so there is no way to associate identity with the record without the user private encryption key. Therefore, subsequently, the medical record access logs can be decrypted from user-record table 812 using the user private encryption key.

Figure 10:
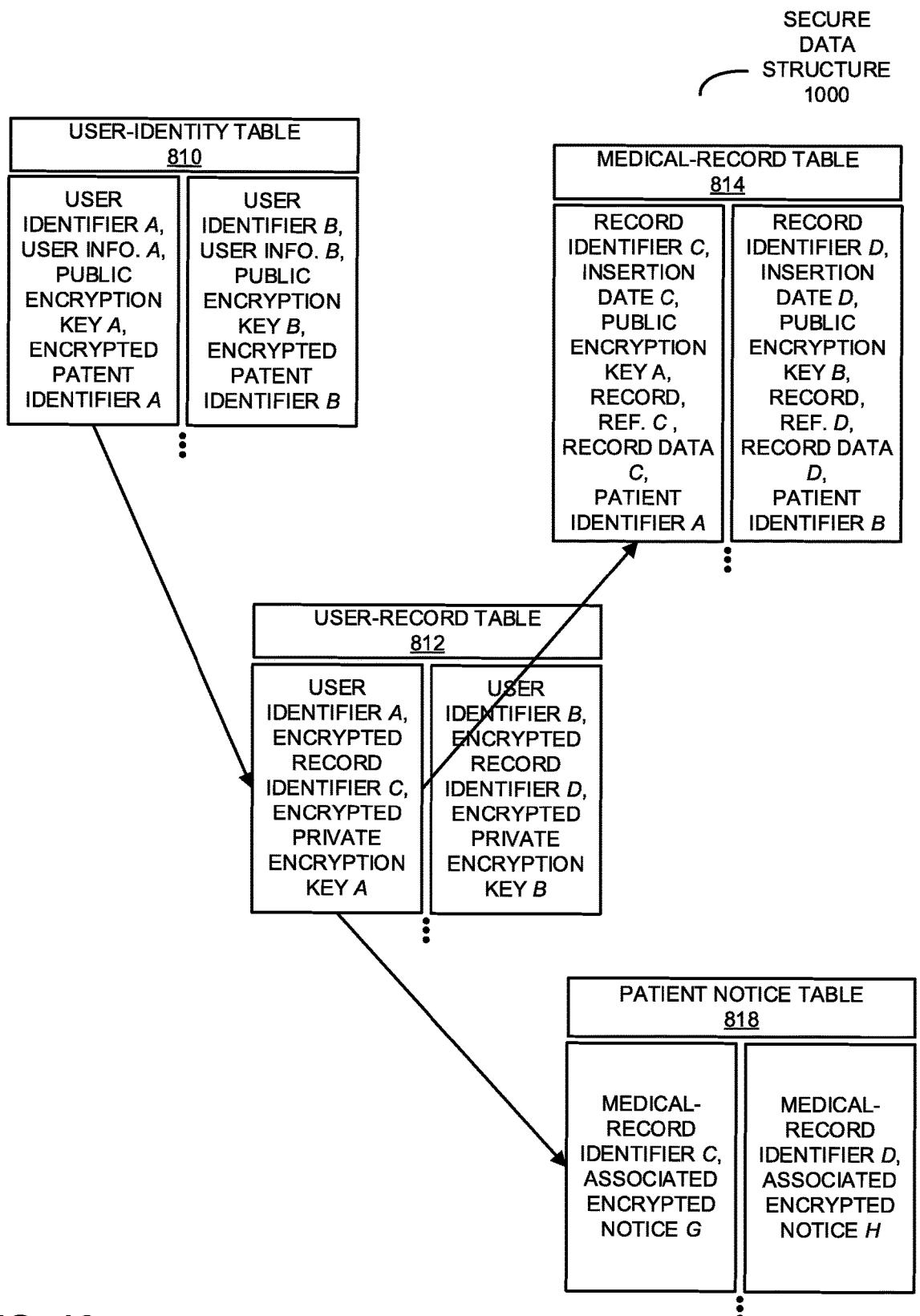
FIG. 10 is a drawing illustrating secure storage of a set of records in the system in FIG. 1 in accordance with an embodiment of the present disclosure.

Similarly, as shown in FIG. 10, which presents a drawing illustrating secure storage of a set of records, secure data structure 1000 may include user-identity table 810, user-record table 812, and medical-record table 814, and a patient-notice table 818. A new notice entry in the patient-notice table 818 may be created every time a notice relating to a medical record/root record is accessed, and the body of the notice entry may be encrypted using the public encryption key associated with the medical record being accessed.

If the computer system needs to alert the user about something (such as when a test result is available), the computer system may need a way to associate this message with a user without knowing who the owner of a given record is. The patient-notice table 818 may only make the patient and record identifiers accessible while keeping the actual message data encrypted. Note that only one of the two identifiers may be required for this operation, but the patient identifier may be optionally included in order to make look-ups faster and this may not compromise security if the patient identifier is already used for other reasons (e.g., linking accessible information from multiple medical records to a patient for researchers with anonymized data access).

The message data, and any attachments, may be encrypted using the public encryption key of the medical record. Because the computer system may not know which user the notice is for, the computer system may not be able to use the public encryption key associated with the user. Instead, the computer system may use the public encryption key associated with the medical record. Therefore, only the intended user may have access to the private encryption key associated with the medical record required to view the notice.

The entries in the patient-notice table 818 may include a medical-record identifier (e.g., to identify which medical record the notice is associated with), and optionally, a patient identifier can be stored in the user-identity table 810, encrypted using the user's public encryption key, and which can be decrypted by the user's private encryption key, which can enable faster look-ups of medical records or notices. Note that the patient identifier, which can be used to identify the patient that the notice is associated with, if used, can only be decrypted from an entry in the user-identity table 810 using a user's private encryption key, so the user must be authorizing such a faster look-up operation.

In some embodiments, the patient notices include system-generated messages, such as: notifications of derivative records or reference records. For example, a derivative record may include: a new result from a blood test, a new result based on research related to a recent blood pressure result, a new animated image of a patient's knees compiled from their last four MRI scans, etc. The derivative records can be based on automated analysis of medical records, updates from doctors, specialists, radiologists or other practitioners, or any other suitable source. Note that the notices can be automatically generated for medical records, and each notice can be encrypted using the public encryption key of the associated medical record.

In embodiments where a patient identifier is not used to speed up the look-up process of providing notices to a patient, a user's private encryption key can be used to decrypt the encrypted record identifiers and their corresponding private encryption keys that are associated with the medical record for the notice. After the private encryption key associated with the medical record is decrypted by the user's private encryption key, then any encrypted notices (or similarly, individual-medical record access logs, as described previously with reference to FIG. 9) associated with the medical-record identifier can be decrypted using the decrypted private encryption key associated with the medical record.

Figure 11:
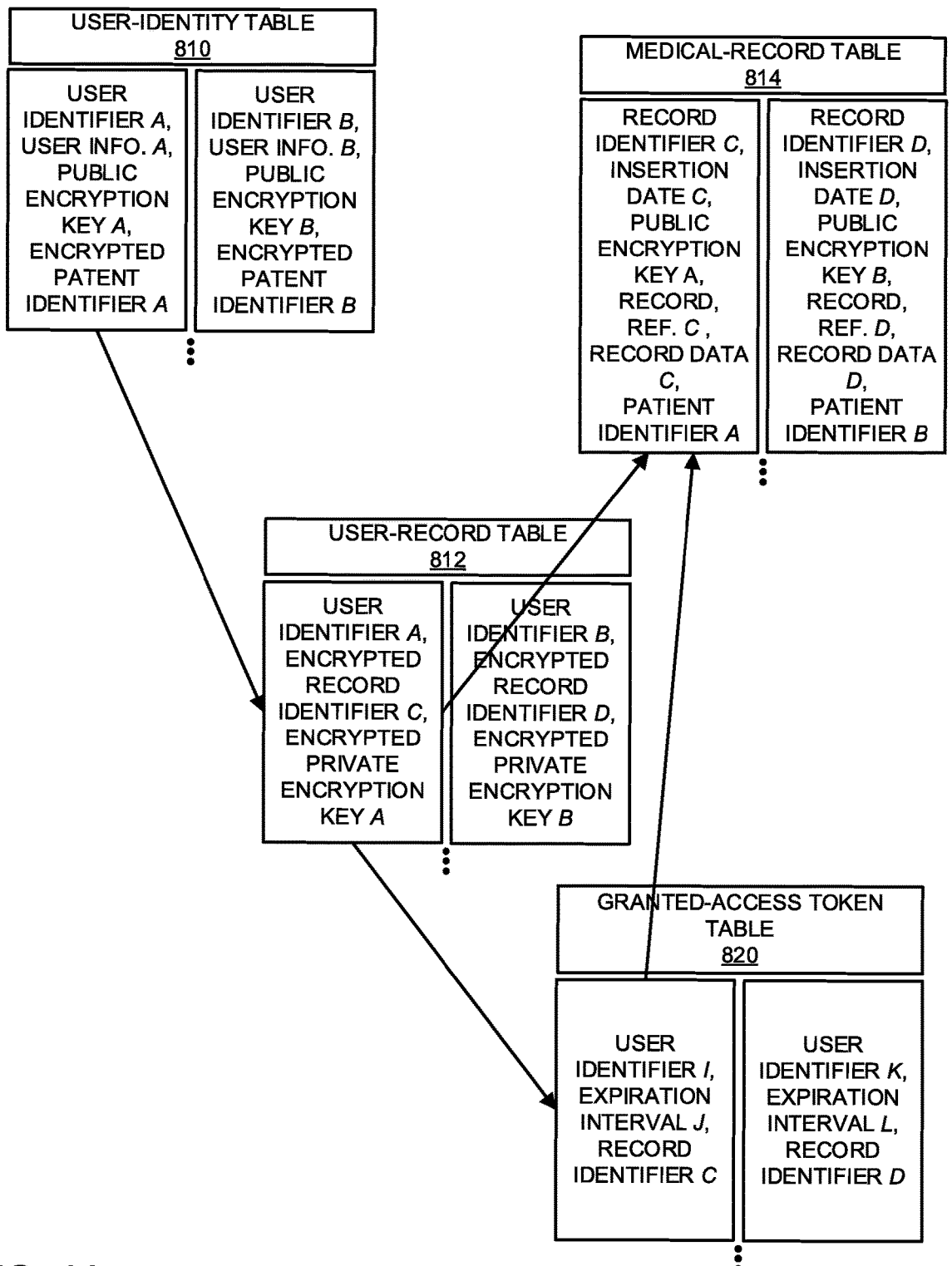
FIG. 11 is a drawing illustrating secure storage of a set of records in the system in FIG. 1 in accordance with an embodiment of the present disclosure.

Moreover, as shown in FIG. 11, which presents a drawing illustrating secure storage of a set of records, secure data structure 1100 may include a user-identity table 810, a user-record table 812, and a medical-record table 814, and a granted-access token table 820. The granted-access token table 820 may create new access tokens in the granted-access token table 820 every time a new access token is created. Furthermore, the granted-access token table 820 may also delete access tokens in the granted-access token table 820 every time an access token expires.

In some embodiments, separating or distinguishing anonymized access for research purposes from access by users is facilitated by an access token. The access token may describe or specify the accessible records, the expiration of the grant, and any other privileges, such as the ability to re-share the record with another professional.

Several approaches and techniques may be used for the token. In some embodiments, the token includes a JavaScript Object Notation (JSON) Web Tokens (JWT). However, a variety of cryptographically signed message formats (such as s/mime) can be used.

A JWT is a cryptographically signed JSON object. In some embodiments, the computer system embeds a record identifier, as well as any other grant information, into the token. Then, the comparer system may sign the JWT using the private encryption key associated with the medical record to which access is being granted (after it is decrypted from user-record table 812), so the JWT can be verified and cannot be modified. Moreover, the private encryption key associated with the medical record to which access is being granted may be used to generate/sign an access token for a user identifier, which can provide access for a user who is associated with the medical record (e.g., if they want to view their own records). Alternatively, if the user wishes to share the medical record with another user or party (e.g., their doctor, or perhaps a relative), they can share access with the other user or party using the JWT by specifying a different user identifier.

For example, if a patient wants to send the results of an MR scan to their primary care doctor, the user may do so by specifying the medical record and the recipient (their doctor in this case) using an application or another software program executing on their electronic device. The application or the software program may use the private encryption key associated with this medical record to create or generate an access token specifying that the doctor (using the doctor's user identifier) can access the medical-record identifier (as well as it's decedents, derivative records, record references, etc.) during a time or expiration interval (such as 30 days). However, the doctor may not share the data with anyone else. The generated access token for the doctor can then be attached to a user record associated with the doctor. Furthermore, a software program executing on the doctor's electronic device or client may use this access token to request the record from the computer system and may present it for review. Note that the computer system may: verify the access token against the public encryption key associated with the medical record (i.e., that the access token was signed using the private encryption key associated with the medical record), serve the requested record data, and store the access information in the access log for this medical record. In some embodiments, the access token is encrypted using the public encryption key of the doctor, and the doctor may use their private encryption key to decrypt the access token before use.

The access from each token may be logged (as shown and described in FIG. 9), and any access based on a token may also include grant information from the token (but not the signature, so the token cannot be re-used). Note that the access log may then be encrypted using the public encryption key associated with the medical record.

Figure 12:
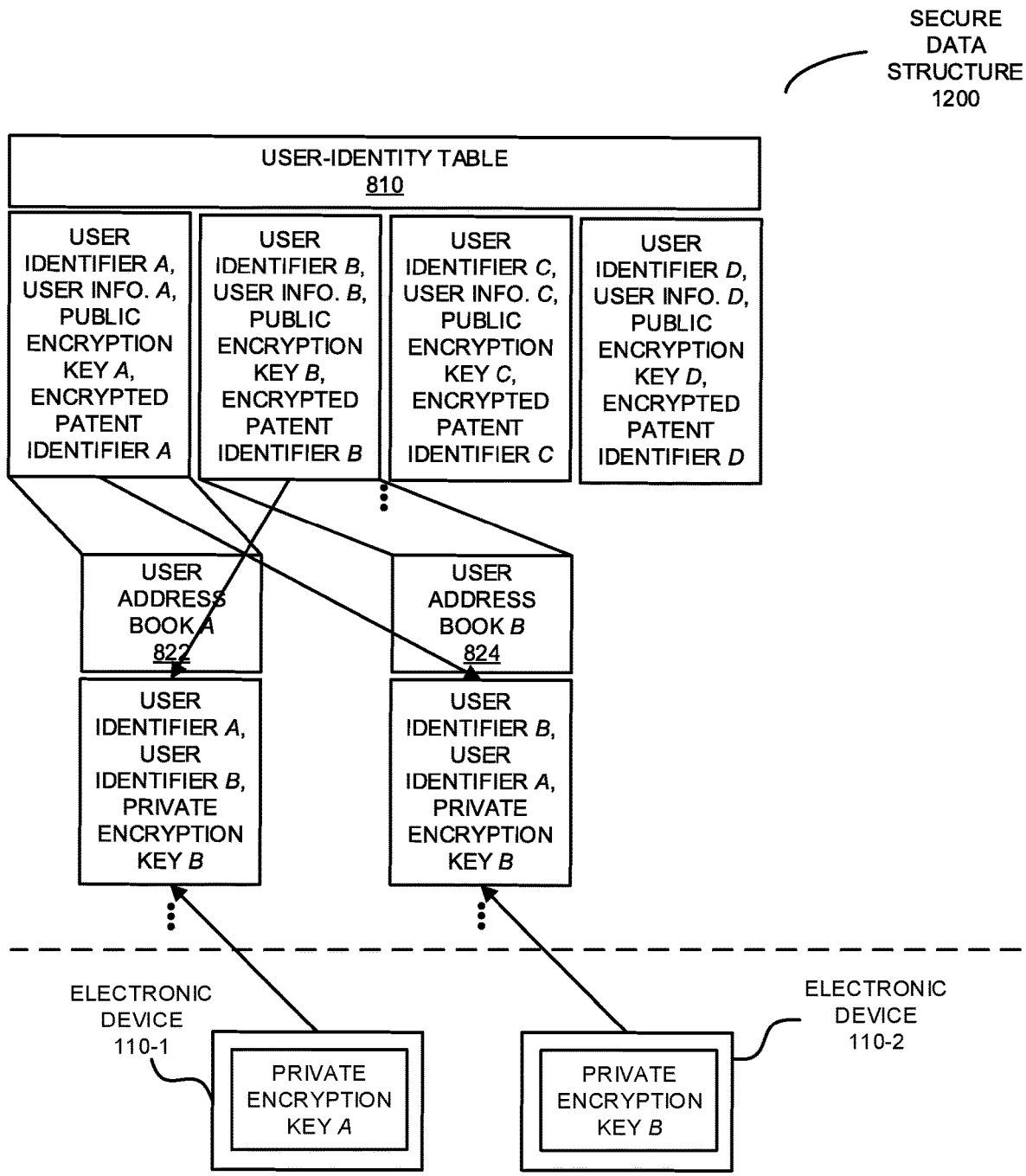
FIG. 12 is a drawing illustrating secure storage of a set of records in the system in FIG. 1 in accordance with an embodiment of the present disclosure.

As shown in FIG. 12, which presents a drawing illustrating secure storage of a set of records, secure data structure 1200 may include a user-identity table 810, a user-record table 812, and a medical-record table 814, a user address book 822, and a user address book 824. The address books of both the first user and the second user may be encrypted using the respective or corresponding public encryption key for each user (thus, the user address book of a given user may be encrypted using their public encryption key). In some embodiments, address books 822 and 824 may be stored in the user-identity table 810, and may be encrypted with the public encryption key associated with each user. Moreover, address books 822 and 824 may then be decrypted using the private encryption key associated with each user when requested (which is similar to how the previously discussed patient identifier is stored in the user-identity table 810). Furthermore, each user may store and decrypt their encrypted address book locally on their electronic device(s) using their private encryption key.

The purpose of address books 822 and 824 may be to prevent a user from arbitrarily looking up any other user in the computer system for privacy reasons. Instead, the user may have an encrypted address book of verified contacts. This verification process may occur in person, using a device-to-device token exchange, and/or using handshaking or other techniques known to those skilled in the art. As a user adds another person to their secure directory/address book, e.g., in person, each user may share their user identifier and public encryption key, as well as other optional information (such as their full name, nickname, identification number, geolocation, medical specialty for doctors, a type of condition for patients, etc.) with the other. In some embodiments, a two-factor authentication code or a verification code (or codes) is sent from a third party server or from a medical-record management system to one or both users to ensure the transaction of adding each user to the other's address book is valid. Note that, depending on the trust between the users, and the security level required for the application, the address book may not need to be secured/encrypted. However, the encryption may provide an additional layer of security.

During a transaction, each user may verify that the public encryption key they are giving to the other party is, in fact, their own, using their private encryption key, and this authorization may also be used to create access tokens for the newly added user in their address book at any time in the future after the users are in each other's address books. After exchanging the public encryption keys, the users may be able to send encrypted messages back and forth (which is described further below).

For example, electronic device 110-1 of a first user A and electronic device 110-2 of a second user B may, respectively (and which are external to secure data structure 1200), include the first user's private encryption key and the second user's private encryption key, and each user's private encryption key may be encrypted, and decrypted based on a biometric identifier provided by a biometric sensor (such as a fingerprint scanner, a retina scanner and/or another suitable biometric device) or a password entered using a user interface on a given electronic device. Note that, once the first user and the second user are in each other's address books, they may be able to subsequently generate access tokens for each other.

In some embodiments, a first user and a second user may exchange their respective user public encryption keys in their address books, and the first user and the second user may each encrypt their address books with their respective public encryption keys. Then, the first user may use electronic device 110-1 to execute a program module or an application to create a message to send to the second user and may encrypt the message with the public encryption key of the second user (after decrypting their address book with the first user's private encryption key. Next, electronic device 110-1 may store the encrypted message (from the first user to the second user) on the computer system, such as in message table 826. The second user may use electronic device 110-2 to execute a program module or an application to query the computer system using or based on the second user's user identifier. In response, electronic device 110-2 may receive matching results, including encrypted messages from the computer system, and may electronic device 110-2 may optionally display a notification or an inbox status message to the second user on a display. Moreover, electronic device 110-2 may request biometric data (such as from a biometric sensor) or a password input (such as via a touch-sensitive display) from the second user. Furthermore, electronic device 110-2 may decrypt the second user's private encryption key with the biometric data or the password, and then may decrypt the message from the first user using the decrypted private encryption key of the second user. Additionally, electronic device 110-2 may display the decrypted notice on the display.

Figure 13:
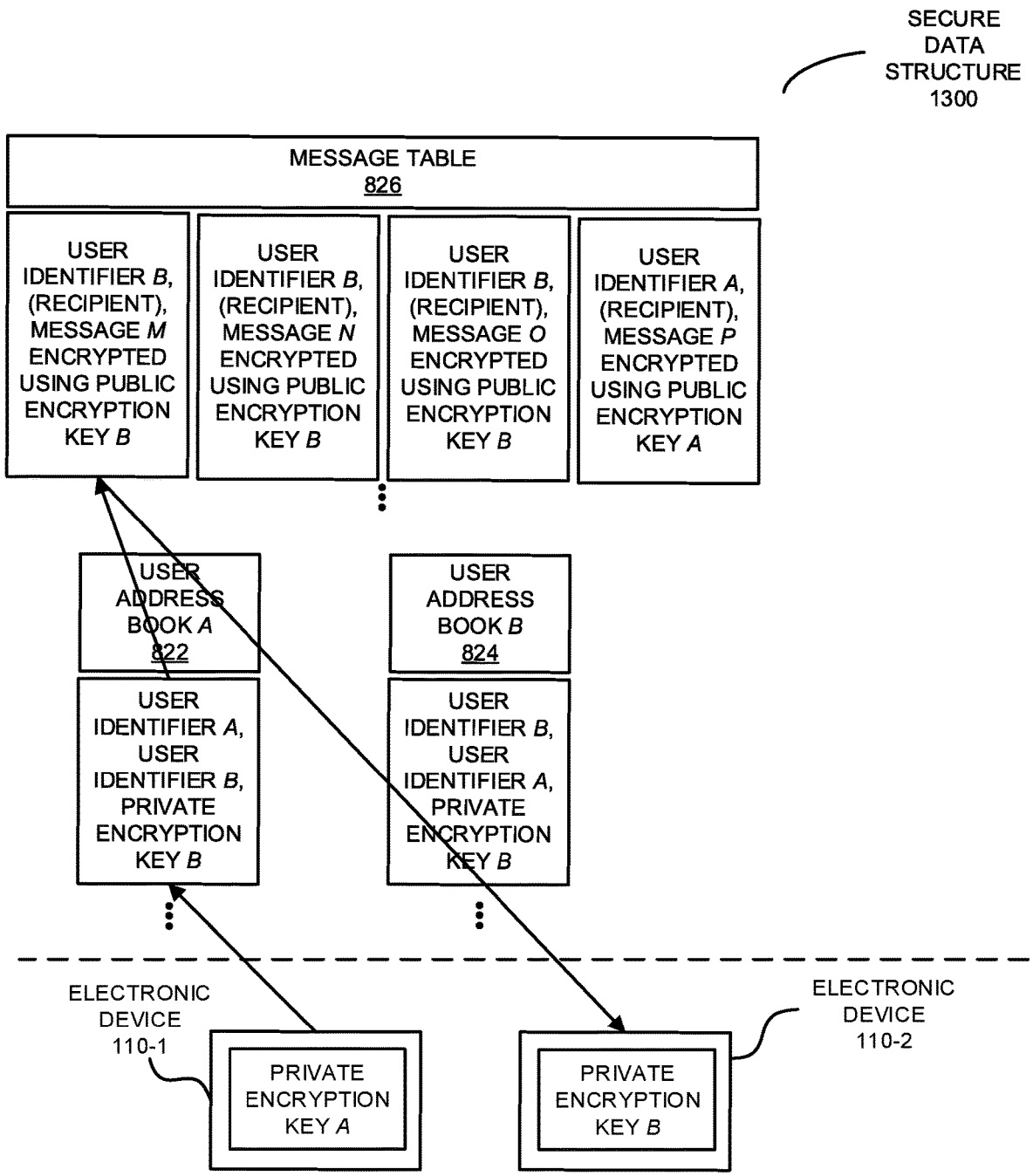
FIG. 13 is a drawing illustrating secure storage of a set of records in the system in FIG. 1 in accordance with an embodiment of the present disclosure.

As shown in FIG. 13, which presents a drawing illustrating secure storage of a set of records, secure data structure 1300 may include a user-identity table 810, a user-record table 812, and a medical-record table 814, and a message table 826. Because one of the functions of the computer system is to allow a user to share their data with a medical professional (e.g., another user, possibly with additional privileges), the computer system may implement messaging in a way that facilitates the sharing of the data without compromising the privacy concerns. For example, in principle a non-trusted third party could derive, based on a user's interaction with an oncologist, critical information about that user or that, user's medical history. The message table 826 may allow a message to be delivered securely because everything about the message is encrypted using the receiver's public encryption key. Note that the field 'Access Tokens' may include references to specific medical records the receiver is intended or allowed to access.

For example, a first user A may send a message to a second user B who is in their encrypted address book (as described previously with reference to FIG. 12). The first user may decrypt their encrypted address book and may select the user they wish to message. Based on the security level required for the application, the address book may not need to be secured/encrypted. However, in some embodiments such encryption may provide an additional layer of security. Then, the first user may create a message (e.g., on the first user's electronic device 110-1) and may encrypt the message body with the second user's public encryption key, which can be decrypted from the first user's encrypted address book using the first user's private encryption key. The message may then be transmitted from the first user's electronic device 110-1 to the computer system, and secure data structure 1200 may store the encrypted message in message table 826 indexed by the user identifier of the second user. (As in FIG. 12, note that electronic devices 110 may be external to secure data structure 1300.) Moreover, the second user may fetch encrypted messages for their user identifier by querying message table 826 in the computer system using their user identifier, and then receiving the matching results, including encrypted messages associated with their user identifier on the second user's electronic device 110-2. Note that the second user's electronic device 110-2 may capture a biometric input or identifier or a password input from the second user to decrypt the second user's private encryption key, and then the second user may decrypt the encrypted messages addressed to the second user using the second user's private encryption key. Note that the messages may include: access tokens granting access to specific medical records, requests for processing, requests for procedures, and requests for scheduling, comments from doctors, specialists, radiologists, or other practitioners, etc.

Thus, a notice relating to a medical record can be generated by the first user using electronic device 110-1, and the generated notice can be encrypted (e.g., by the computer system) using the public encryption key associated with the associated medical record of the second user. Subsequently, electronic device 110-2 may request biometric data (such as from a biometric sensor) or a password input (such as via a touch-sensitive display) and may decrypt the second user's private encryption key based on the biometric data or the password. Next, electronic device 110-2 may poll the computer system based on the second user's user identifier. In response, electronic device 110-2 may receive encrypted record identifiers and encrypted record private encryption keys associated with the user identifier from the computer system. Moreover, electronic device 110-2 may decrypt the private encryption key(s) and record identifier(s) associated with the medical record using the decrypted user private encryption key. Furthermore, electronic device 110-2 may query the computer system using the decrypted record identifier(s) and may receive matching results, including the encrypted notices (or access logs) associated with the medical-record identifier(s). Using the decrypted private encryption key (which is associated with the medical record), electronic device 110-2 may decrypt the encrypted notices (or access logs) associated with the medical record, and then electronic device 110-2 may display the decrypted notice on a display. Note that a similar process can be used to enable users to view access logs (such as based on a patient identifier) because they may be encrypted, handled, and stored in almost identical fashion.

In some embodiments, messages and notifications are communicated anonymously between the computer system and the users using a secure interface. This is shown in FIG. 14, which presents a drawing illustrating a secure interface 1400 for communicating Information in system 100 (FIG. 1). This secure interface may implement a secure join 1410 between a user message space 1412 and a computer-system message space 1414. Input notifications or messages 1416 from the computer system may be encrypted using user's public encryption keys based on user identifiers or patient identifiers. Moreover, secure interface 1400 may perform a one-way mapping to output notifications or messages 1418 to eliminate traceable edges during the communication. Furthermore, fake notifications or messages may also be generated and accessed (for example, using an automated agent or computer), so that the pattern or frequency of occurrence of the communication is uniform.

We now describe embodiments of an electronic device. FIG. 15 presents a block diagram illustrating an electronic device 1500, such as one of electronic devices 110 or computer system 118 in FIG. 1. This electronic device includes processing subsystem 1510, memory subsystem 1512, and networking subsystem 1514. Processing subsystem 1510 includes one or more devices configured to perform computational operations. For example, processing subsystem 1510 can include one or more microprocessors, application-specific integrated circuits (ASICs), microcontrollers, programmable-logic devices, and/or one or more digital signal processors (DSPs).

Memory subsystem 1512 includes one or more devices for storing data and/or instructions for processing subsystem 1510 and networking subsystem 1514. For example, memory subsystem 1512 can include dynamic random access memory (DRAM), static random access memory (SRAM), and/or other types of memory. In some embodiments, instructions for processing subsystem 1510 in memory subsystem 1512 include: one or more program modules or sets of instructions (such as program module 1522 or operating system 1524), which may be executed by processing subsystem 1510. Note that the one or more comparer programs may constitute a computer-program mechanism. Moreover, instructions in the various modules in memory subsystem 1512 may be implemented in: a high-level procedural language, an object-oriented programming language, and/or in an assembly or machine language. Furthermore, the programming language may be compiled or interpreted, e.g., configurable or configured (which may be used interchangeably in this discussion), to be executed by processing subsystem 1510.

In addition, memory subsystem 1512 can include mechanisms for controlling access to the memory. In some embodiments, memory subsystem 1512 includes a memory hierarchy that comprises one or more caches coupled to a memory in electronic device 1500. In some of these embodiments, one or more of the caches is located in processing subsystem 1510.

In some embodiments, memory subsystem 1512 is coupled to one or more high-capacity mass-storage devices (not shown). For example, memory subsystem 1512 can be coupled to a magnetic or optical drive, a solid-state drive, or another type of mass-storage device. In these embodiments, memory subsystem 1512 can be used by electronic device 1500 as last-access storage for often-used data, while the mass-storage device is used to store less frequently used data.

Figure 15:
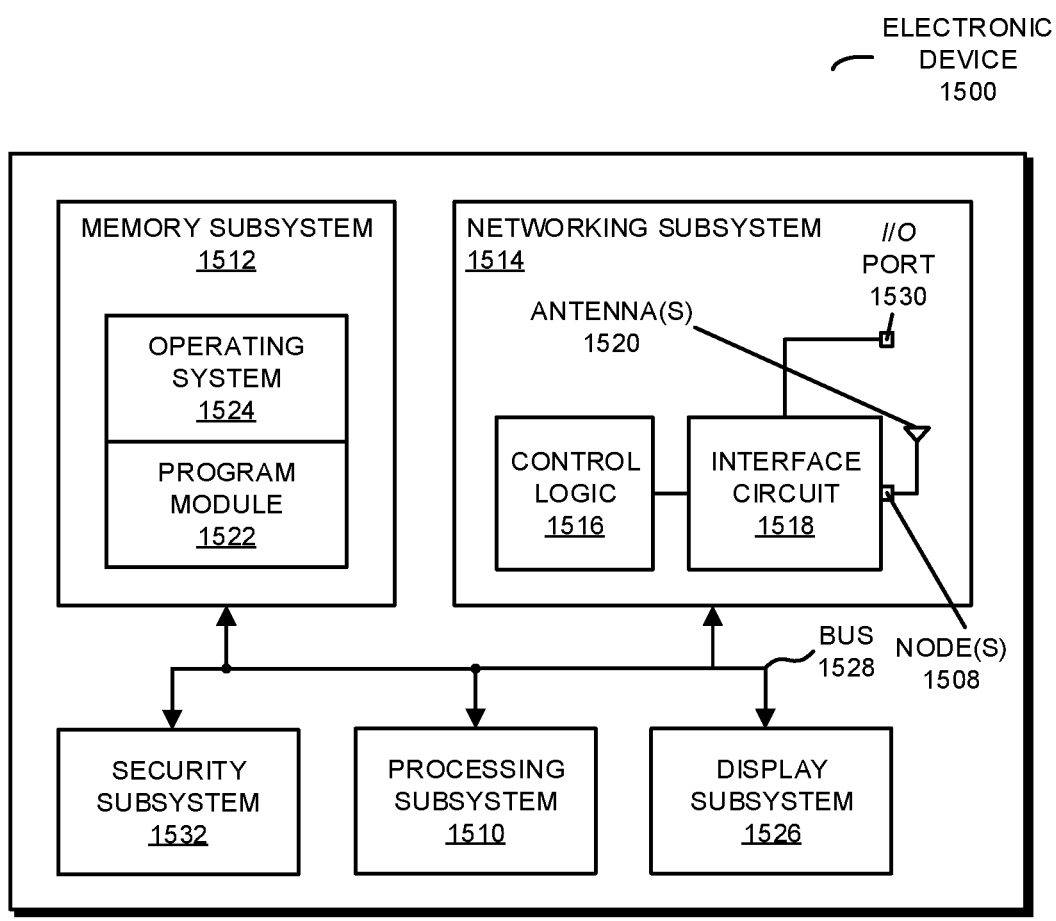
FIG. 15 is a block diagram illustrating electronic device in the system of FIG. 1 in accordance with an embodiment of the present disclosure.

While FIG. 15 illustrates electronic device 1500 as including memory subsystem 1512, in some embodiments memory subsystem 1512 includes remotely accessible memory, such as: a cloud-based storage system, a high-capacity network attached mass-storage device (e.g., network attached storage), an external hard drive, a magnetic-tape backup system, a medical records archive service, or any other suitable archive devices.

In some embodiments, blocks of data are stored in memory subsystem 1512 using a blockchain or similar cryptographic hash technology to detect unauthorized modification or corruption of records. Moreover, the data can be anonymized so that the identity associated with a subject is anonymous unless the subject gives permission or authorization for this information to be released.

Networking subsystem 1514 may include one or more devices configured to couple to and communicate on a wired and/or wireless network (i.e., to perform network operations), including: control logic 1516, an interface circuit 1518, one or more antennas 1520 and/or input/output (I/O) port 1530. (While FIG. 15 includes one or more antennas 1520, in some embodiments electronic device 1500 includes one or more nodes 1508, e.g., a pad, which can be coupled to one or more antennas 1520. Thus, electronic device 1500 may or may not include one or more antennas 1520.) For example, networking subsystem 1514 can include a Bluetooth networking system, a cellular networking system (e.g., a 3G/4G network such as UMTS, LTE, etc.), a universal serial bus (USB) networking system, a networking system based on the standards described in IEEE 802.11 (e.g., a Wi-Fi networking system), an Ethernet networking system, and/or another networking system.

Networking subsystem 1514 includes processors, controllers, radios/antennas, sockets/plugs, and/or other devices used for coupling to, communicating on, and handling data and events for each supported networking system. Note that mechanisms used for coupling to, communicating on, and handling data and events on the network for each network system are sometimes collectively referred to as a 'network interface' for the network system. Moreover, in some embodiments a 'network' between the electronic devices does not yet exist. Therefore, electronic device 1500 may use the mechanisms in networking subsystem 1514 for performing simple wireless communication between the electronic devices, e.g., transmitting advertising or beacon frames and/or scanning for advertising frames transmitted by other electronic devices as described previously.

Within electronic device 1500, processing subsystem 1510, memory subsystem 1512, and networking subsystem 1514 are coupled together using bus 1528. Bus 1528 may include an electrical, optical, and/or electro-optical connection that the subsystems can use to communicate commands and data among one another. Although only one bus 1528 is shown for clarity, different embodiments can include a different number or configuration of electrical, optical, and/or electro-optical connections among the subsystems.

In some embodiments, electronic device 1500 includes a display subsystem 1526 for displaying information on a display, which may include a display driver and the display, such as: a liquid-crystal display, a multi-touch touchscreen or a touch-sensitive display, an optical projector, a laser projector, a holographic display, or any other suitable display for displaying 2-dimensional or 3-dimensional images.

Moreover, electronic device 1500 may include a security subsystem 1532, which may include one or more biometric sensor(s) and/or may implement password authorization. For example, the one or more biometric sensors may include: a fingerprint scanner, a retina scanner, and/or another biometric sensor that can capture biometric information that is used for authentication and/or authorization.

Electronic device 1500 can be (or can be included in) any electronic device with at least one network interface. For example, electronic device 1500 can be (or can be included in): a desktop computer, a laptop computer, a subnotebook/netbook, a server, a workstation, a tablet computer, a smartphone, a cellular telephone, a smart watch, a consumer-electronic device, a portable computing device, an access point, a router, a switch, communication equipment, test equipment, a security camera, an aviation drone, a nanny camera, a wearable appliance, and/or another electronic device.

Although specific components are used to describe electronic device 1500, in alternative embodiments, different components and/or subsystems may be present in electronic device 1500. For example, electronic device 1500 may include one or more additional processing subsystems, memory subsystems, networking subsystems, display subsystems and/or audio subsystems. Additionally, one or more of the subsystems may not be present in electronic device 1500. Moreover, in some embodiments, electronic device 1500 may include one or more additional subsystems that are not shown in FIG. 15. Also, although separate subsystems are shown in FIG. 15, in some embodiments, some or all of a given subsystem or component can be integrated into one or more of the other subsystems or component(s) in electronic device 1500. For example, in some embodiments program module 1522 is included in operating system 1524.

Moreover, the circuits and components in electronic device 1500 may be implemented using any combination of analog and/or digital circuitry, including: bipolar, PMOS and/or NMOS gates or transistors. Furthermore, signals in these embodiments may include digital signals that have approximately discrete values and/or analog signals that have continuous values. Additionally, components and circuits may be single-ended or differential, and power supplies may be unipolar or bipolar.

An integrated circuit may implement some or all of the functionality of networking subsystem 1514, such as a radio. Moreover, the integrated circuit may include hardware and/or software mechanisms that are used for transmitting wireless signals from electronic device 1500 and receiving signals at electronic device 1500 from other electronic devices. Aside from the mechanisms herein, described, radios are generally known in the art and hence are not described in detail. In general, networking subsystem 1514 and/or the integrated circuit can include any number of radios. Note that the radios in multiple-radio embodiments function in a similar way to the described single-radio embodiments.

In some embodiments, networking subsystem 1514 and/or the integrated circuit include a configuration mechanism (such as one or more hardware and/or software mechanisms) that configures the radio(s) to transmit and/or receive on a given communication channel (e.g., a given carrier frequency). For example, in some embodiments, the configuration mechanism can be used to switch the radio from monitoring and/or transmitting on a given communication channel to monitoring and/or transmitting on a different communication channel (Note that 'monitoring' as used herein comprises receiving signals from other electronic devices and possibly performing one or more processing operations on the received signals, e.g., determining if the received signal comprises an advertising frame, receiving the Input data, etc.)

While communication protocols compatible with Ethernet and Wi-Fi or a cellular-telephone communication protocol were used as illustrative examples, the described embodiments of the security technique may be used in a variety of network interfaces. Furthermore, while some of the operations in the preceding embodiments were implemented in hardware or software, in general the operations in the preceding embodiments can be implemented in a wide variety of configurations and architectures. Therefore, some or all of the operations in the preceding embodiments may be performed in hardware, in software or both. For example, at least some of the operations in the security technique may be implemented using program module 1522, operating system 1524 (such as a driver for interface circuit 1518) and/or in firmware in interface circuit 1518. Alternatively or additionally, at least some of the operations in the security technique may be implemented in a physical layer, such as hardware to interface circuit 1518.

While program module 1522 is illustrated as being resident on and executed by electronic device 1500, in some embodiments a user of electronic device 1500 may interact with a web page that is provided by another electronic device, and which is rendered by a web browser on electronic device 1500. In some embodiments, at least a portion of program module 1522 (such as software or an application) executing on electronic device 1500 may be an application tool that is embedded in the web page, and that executes in a virtual environment of the web browser. Thus, the application tool may be provided to the user via a client-server architecture. Note that program module 1522 executed by electronic device 1500 may be a standalone application or a portion of another application that is resident on and that executes on electronic device 1500.

In the preceding description, we refer to 'some embodiments.' Note that 'some embodiments' describes a subset of all of the possible embodiments, but does not always specify the same subset of embodiments. Moreover, note that the numerical values provided are intended as illustrations of the communication technique. In other embodiments, the numerical values can be modified or changed.

The foregoing description is intended to enable any person skilled in the art to make and use the disclosure, and is provided in the contest of a particular application and its requirements. Moreover, the foregoing descriptions of embodiments of the present disclosure have been presented for purposes of illustration and description only. They are not intended to be exhaustive or to limit the present disclosure to the forms disclosed. Accordingly, many modifications and variations will be apparent so practitioners skilled in the art, and the general principles defined herein may be applied to other embodiments and applications without departing from the spirit and scope of the present disclosure. Additionally, the discussion of dm preceding embodiments is not intended to limit the present disclosure. Thus, the present disclosure is not intended to be limited to the embodiments shown, but is to be accorded the widest scope consistent with the principles and features disclosed herein.

What is claimed is:

1. A method for accessing information in a set of records, comprising:
by a processor:
receiving, via an interface circuit, a request for the information, wherein the request is associated with an electronic device corresponding to an entity;
confirming that the entity is authorized to access the set of records;
recovering the information from a secured set of records, wherein the recovering involves:
removing one or more artificial set of records from the secured set of records, so that at least some phrases or values in the set of records are not uniformly distributed; and
restoring context information in the set of records while maintaining relevance of the set of records by performing substitutions for replacement fields in the set of records, wherein performing a given substitution involves replacing a replacement field in the set of records with a field, and wherein the context information was previously removed from the set of records and corresponds to different fields in the set of records that, at least in part, indirectly identify an individual; and providing, via the interface circuit, the information for the electronic device.

2. The method of claim 1, wherein the field replaces random or pseudorandom alphanumeric information in the replacement fields.

3. The method of claim 1, wherein the recovering involves reordering the set of records, so that the set of records are not randomly or pseudo-randomly ordered.

4. The method of claim 1, wherein the substitutions are predefined.

5. The method of claim 1, wherein the substitutions are determined based on information value of the fields in the set of records.

6. The method of claim 1, wherein the substitutions are determined based on a cardinality of the fields in the set of records.

7. The method of claim 1, wherein the recovering involves reordering additional fields that include timestamps in the set of records.

8. The method of claim 1, wherein the entity includes one of: a patient, a medical provider, and an insurance company.

9. The method of claim 1, wherein the recovering involves modifying imaging data in the set of records based on imaging instructions and an invariant signature that predicts responses of voxels in at least an individual.

10. A non-transitory computer-readable storage medium for use in conjunction with a computer system, the computer-readable storage medium storing a program module that, when executed by the computer system, accesses information in a set of records by causing the computer system to perform one or more operations comprising:

receiving, via an interface circuit in the computer system, a request for the information, wherein the request is associated with an electronic device corresponding to an entity;

confirming that the entity is authorized to access the set of records;

recovering the information from a secured set of records, wherein the recovering involves:

removing one or more artificial set of records from the secured set of records, so that at least some phrases or values in the set of records are not uniformly distributed; and restoring context information in the set of records while maintaining relevance of the set of records by performing substitutions for replacement fields in the set of records, wherein performing a given substitution involves replacing a replacement field in the set of records with a field, and wherein the context information was previously removed from the set of records and corresponds to different fields in the set of records that, at least in part, indirectly identify an individual; and providing, via the interface circuit, the information for the electronic device.

11. The computer-readable storage medium of claim 10, wherein the field replaces random or pseudorandom alphanumeric information in the replacement fields with one or more words or second values.

12. The computer-readable storage medium of claim 10, wherein the recovering involves reordering the set of records, so that the set of records are not randomly or pseudo-randomly ordered.

13. The computer-readable storage medium of claim 10, wherein the substitutions are predefined.

14. The computer-readable storage medium of claim 10, wherein the substitutions are determined based on information value of the fields in the set of records.

15. The computer-readable storage medium of claim 10, wherein the substitutions are determined based on a cardinality of the fields in the set of records.

16. The computer-readable storage medium of claim 10, wherein the recovering involves reordering additional fields that include timestamps in the set of records.

17. The computer-readable storage medium of claim 10, wherein the entity includes one of: a patient, a medical provider, and an insurance company.

18. The computer-readable storage medium of claim 10, wherein the recovering involves modifying imaging data in the set of records based on imaging instructions and an invariant signature that predicts responses of voxels in at least an individual.

19. A computer system, comprising:

an interface circuit;

a processor, coupled to the interface circuit, configured to execute a program module;

memory, coupled to the processor, configured to store the program module, wherein, when executed by the computer system, the program module causes the computer system to access information in a set of records by performing one or more operations comprising:

receiving, via the interface circuit, a request for the information, wherein the request is associated with an electronic device corresponding to an entity;

confirming that the entity is authorized to access the set of records;

recovering the information from a secured set of records, wherein the recovering involves:

removing one or more artificial set of records from the secured set of records, so that at least some phrases or values in the set of records are not uniformly distributed; and restoring context information in the set of records while maintaining relevance of the set of records by performing substitutions for replacement fields in the set of records, wherein performing a given substitution involves replacing a replacement field in the set of records with a field, and wherein the context information was previously removed from the set of records and corresponds to different fields in the set of records that, at least in part, indirectly identify an individual; and providing, via the interface circuit, the information for the electronic device.

20. The computer system of claim 19, wherein the substitutions are determined based on a cardinality of the fields in the set of records.

* * * * *